(12) United States Patent
Voorhees et al.

(10) Patent No.: US 7,361,186 B2
(45) Date of Patent: Apr. 22, 2008

(54) ACTIVE BODY COOLING WITH VASODILATION TO REDUCE BODY TEMPERATURE

(75) Inventors: Marc E. Voorhees, Arvada, CO (US); Judy E. Lawten, Longmont, CO (US); Richard M. Zweifler, Mobile, AL (US)

(73) Assignee: Medivance, Incorporated, Louisville, CO (US)

(*) Notice: Subject to any disclaimer, the term of this patent is extended or adjusted under 35 U.S.C. 154(b) by 114 days.

(21) Appl. No.: 10/926,279

(22) Filed: Aug. 25, 2004

(65) Prior Publication Data

US 2005/0065583 A1 Mar. 24, 2005

Related U.S. Application Data

(60) Provisional application No. 60/560,101, filed on Apr. 7, 2004, provisional application No. 60/497,671, filed on Aug. 25, 2003.

(51) Int. Cl.
*A61F 7/00* (2006.01)
(52) U.S. Cl. .................. 607/104; 607/96; 607/108
(58) Field of Classification Search .......... 607/96–114
See application file for complete search history.

(56) References Cited

U.S. PATENT DOCUMENTS

| 4,149,529 | A | * | 4/1979 | Copeland et al. ............. 601/17 |
| 5,486,204 | A | * | 1/1996 | Clifton ......................... 607/96 |
| 5,637,309 | A | * | 6/1997 | Tajima et al. ................ 424/423 |
| 6,113,626 | A | * | 9/2000 | Clifton et al. ................. 607/96 |
| 6,126,680 | A | * | 10/2000 | Wass ............................ 607/96 |
| 6,197,045 | B1 | * | 3/2001 | Carson ....................... 607/104 |
| 6,231,594 | B1 | * | 5/2001 | Dae ............................. 607/96 |
| 6,375,674 | B1 | * | 4/2002 | Carson ....................... 607/104 |
| 6,468,297 | B1 | * | 10/2002 | Williams et al. ............. 607/113 |
| 6,544,282 | B1 | * | 4/2003 | Dae et al. .................... 607/105 |
| 6,572,638 | B1 | | 6/2003 | Dae et al. ..................... 607/96 |
| 6,582,457 | B2 | | 6/2003 | Dae et al. .................... 607/113 |
| 6,702,839 | B1 | | 3/2004 | Dae et al. ..................... 607/96 |
| 6,743,250 | B2 | * | 6/2004 | Renfro ....................... 607/104 |

OTHER PUBLICATIONS

Alfonsi, P. et al. "The effects of pethidine, fentanyl and lignocaine on postanaesthetic shivering." Anaesthesia. vol. 50, pp. 214-217, 1995.
Alfonsi, P. et al. "The Effects of Meperidine and Sufentanil on the Shivering Threshold in Postopoerative Patients." Anethesiology. vol. 89, No. 1, pp. 43-48. Jul. 1998.
Alfonsi, P. "Postanaesthetic Shivering: Epidemiology, Pathophysiology, and Approaches to Prevention and Management." Drugs. vol. 61, pp. 2193-2205. 2001.
Dawes, Matthew and Ritter, James M. "$Mg^2+$-Induced Vasodilation in Human Forearm Vasculature Is Inhibited by $N^G$-Monomethyl-*L*-Arginine but Not by Indometacin." Journal of Vascular Research. vol. 37, pp. 276-281. 2000.

Doufas, A.G. et al. "Dexmedetomidine and Meperidine Additively Reduce the Shivering Threshold in Humans." Stroke. vol. 34, pp. 1218-1223. 2003.
English, M.M.J. "Heat Exchange Coefficient of the Artic Sun Energy Transfer Pads." 8 pages. 2003.
Prescott, L. M. "Single-Dose Palonosetron Prevents Emesis for as Long as 40 Hours." Anesthesiology News. vol. 29, No. 8. 5 pages. Aug. 2003.
Fugate, S.R. et al. "Eclampsia." www.emedicine.com. EMedicine.com, Inc. 16 pages. 2003.
Gadegbeku, C.A. et al. "Hemodynamic Effects of Nicotinic Acid Infusion in Normotensive and Hypertensive Subjects." The American Journal of Hypertension, Ltd. vol. 16, pp. 67-71. 2003.
Goodin, S. and Cunningham, R. $5-HT_3$-Receptor Antagonists for the Treatment of Nausea and Vomiting: A Reappraisal of Their Side-Effect Profile. The Oncologist. vol. 7, pp. 424-436. 2002.
Guffin, A. et al. Shivering Following Cardiac Surgery: Hemodynamic Changes and Reversal. Journal of Cardiothoracic Anesthesia. vol. 1, No. 1. pp. 24-28. Feb. 1987.
Ikeda, T. et al. "The Effect of Opioids on Thermoregulatory Responses in Humans and the Special Antishivering Action of Meperidine." Annals New York Academy of Sciences. 15;813: pp. 792-798. 1997.
Ikeda, T. et al. "Meperidine and Alfentanil Do Not Reduce the Gain or Maximum Intensity of Shivering." Anesthesiology. vol. 88, No. 4, pp. 858-865. Apr. 1998.
Katzman, M. et al. "Methyl Nicotinate-Induced Vasodilation in Generalized Social Phobia." Neuropsychopharmacology. vol. 28, pp. 1846-1851. 2003.
Kawamura, S. et al. "Hypothermia Bed System for Stroke Patients." Neurol Med Chir (Tokyo). vol. 39, pp. 466-470. 1999.
Kizilirmak, S. et al. "Magnesium Sulfate Stops Postanesthetic Shivering." Annals of the New York Academy of Sciences. vol. 813, pp. 799-806. Mar. 15, 1997.
Knoll, T. et al. "The Low Normothermia Concept—Maintaining a Core Body Temperature Between 36 and 37° C. in Acute Stroke Unit Patients." Journal of Neurosurgical Anesthesiology. vol. 14, No. 4, pp. 304-308. 2002.
Kranke, P. et al. "Pharmacological Treatment of Postoperative Shivering: A Quantitative Systematic Review of Randomized Controlled Trials." Anesth Analg. vol. 94. pp. 453-460. 2002.
Kurz, A. et al. "Thermoregulatory Vasoconstriction Impairs Active Core Cooling." Anesthesiology. vol. 82, No. 4, pp. 870-876. 1995.
Kurz, A. et al. "Meperidine Decreases the Shivering Threshold Twice as Much as the Vasoconstriction Threshold." Anesthesiology. vol. 86, No. 5, pp. 1046-1054. May 1997.
Kyriakides, K. et al. "Management of opiod-induced pruritus: a role for $5-HT_3$ antagonists?" British Journal of Anaesthesia. vol. 82, pp. 439-441. 1999.
"Meperdine". Clinical Pharmacology. 25 pages. 2000.
Mokhtarani, M. et al. "Buspirone and Meperidine Synergistically Reduce the Shivering Threshold." vol. 93, pp. 1233-1239. 2001.

(Continued)

Primary Examiner—Roy D. Gibson
(74) Attorney, Agent, or Firm—Marsh Fischmann & Breyfogle LLP

(57) ABSTRACT

Active cooling of a person, such as to induce mild/moderate hypothermia, is accomplished by transferring heat from the persons body. Heat transfer and patient comfort are aided by administration of an anti-shivering drug and an anti-emetic drug.

32 Claims, 23 Drawing Sheets

OTHER PUBLICATIONS

Morrow, J.D. et al. "Identification of Skin as a Major Site of Prostaglandin D2 Release Following Oral Administration of Niacin in Human." vol. 98, No. 5, pp. 812-815. 1992.

Muir, K.W. "Magnesium in stroke treatment." Postgrad Med J. vol. 78, pp. 641-645. 2002.

Olson, James M. *Clinical Pharmacology Made Ridiculously Simple*. MedMaster, Inc. pp. 30, 31, 52-55. 1998.

Pauca, A.L. et al. "Effect of Pethidine, Fentanyl and Morphine on Post-Operative Shivering in Man." Acta Anaesthesiol Scand. vol. 28, pp. 138-143. 1984.

Powell, R.M. and Buggy, D.J. "Ondansetron Given Before Induction of Anesthesia Reduces Shivering After General Anesthesia." Anesth Analg. vol. 90, pp. 1423-1427. 2000.

Schmid-Elsaesser, R. et al. "Combination Drug Therapy and Mild Hypothermia A Promising Treatment Strategy for Reversible, Focal Cerebral Ischemia." Stroke. vol. 30, pp. 1891-1899. Sep. 1999.

Svedmyr, N. et al. "The relationship between the plasma concentration of free nicotinic acid and some of its pharmacologic effects in man." Clinical Pharmacology and Therapeutics. vol. 10, No. 4, pp. 559-570. 1969.

Suleman, M.I. et al. "Dexmedetomidine and Meperidine Additively Reduce the Shivering Threshold." Anesthesiology. vol. 96, p. A-311. 2002.

Wilkin, J.K. et al. "Prostaglandins and nicotinate-provoked increase in cutaneous blood flow." Clin Pharmacol. Ther. vol. 38, No. 3, pp. 273-277. Sep. 1985.

"ZOFRAN® (ondansetron hydrochloride) Injection ZOFRAN® (ondansetron hydrochloride) Injection Premixed." Product Information. GlaxoWellcome Inc. 19 pages. 2000.

"ZOFRAN® (ondansetron hydrochloride) Tablets ZOFRAN® (ondansetron). Orally Disintegrating Tablets ZOFRAN® (ondansetron hydrochloride) Oral Solution." Product Information. GlaxoSmithKline. 14 pages. 2001.

Zweifler, R.M. and Sessler, D.I. "Thermoregulatory Vasoconstriction and Shivering Impede Therapeutic Hypothermia in Acute Ischemic Stroke Patients." Journal of Stroke and Cerebrovascular Diseases. vol. 6, No. 2, pp. 100-104. 1996.

Zweifler, R.M. et al. "Induction and Maintenance of Mild Hypothermia by Surface Cooling in Non-intubated Subjects." Journal of Stroke and Cerebrovascular Diseases. vol. 12, No. 5. pp. 237-243. 2003.

Zweifler, R.M. et al. "Magnesium Sulfate Increases the Rate of Hypothermia Via Surface Cooling and Improves Comfort." Stroke. vol. 35, pp. 2331-2334. 2004.

Zweifler, R.M. et al. "A Novel Method to Induce Mild Hypothermia Via Surface Cooling." American Academy of Neurology 53rd Annual Meeting, Philadelphia, Pennyslvania, May 5-11, 2001. 5 pages.

* cited by examiner

ACTIVE BODY COOLING WITH VASODILATION TO REDUCE BODY TEMPERATURE

CROSS-REFERENCE TO RELATED APPLICATIONS

This application claims priority under 35 U.S.C. § 119 to each of prior U.S. Provisional Patent Application No. 60/497,671, filed Aug. 25, 2003, entitled "ACTIVE BODY COOLING WITH VASODILATION TO REDUCE BODY TEMPERATURE", and U.S. Provisional Patent Application No. 60/560,101, filed Apr. 7, 2004, entitled "ACTIVE BODY COOLING WITH VASODILATION TO REDUCE BODY TEMPERATURE", the entire contents of each of which are incorporated herein by reference as if each were set forth herein in full.

FIELD OF THE INVENTION

The invention relates to rapid inducement of hypothermia for therapeutic purposes.

BACKGROUND OF THE INVENTION

Hypothermia is a condition in which body temperature is at a level lower than normal body temperature. Therapeutic induced mild-moderate hypothermia can be beneficial for people suffering stroke, myocardial infarction, cardiac arrest and other conditions involving reduced blood supply. One method for lowering body temperature is to insert a cooling device into an artery of the patient and to internally cool the patient's body by introducing a cooling fluid into the device. One concern for such endovascular techniques is the invasive nature of the procedure. A non-invasive technique for lowering body temperature is to externally cool the exterior surface of the patient's body. Such exterior surface cooling could be achieved, for example by direct contact with a cooling fluid, such as by immersing the patient's body in the cooling fluid or by directing the flow of the cooling fluid around the patient's body. The cooling fluid could be, for example, cool water or cool air. Another technique for external surface cooling is to apply a contact-cooling pad to the exterior surface of the patient and to circulate a cooling fluid, such as water or an aqueous solution, through the contact pad to cool the patient.

For therapeutic purposes, it is often desirable for the mild-moderate hypothermia to be induced very quickly. With endovascular cooling, heat is removed directly from blood flowing through blood vessels via a heat exchange device that is inserted into the vasculature. Blood with reduced temperature moves through blood vessels to cool other parts of the body. Conversely, with exterior surface cooling, heat is removed across the patient's skin. Cooling of the skin increases conduction of heat from deeper within the body, thereby cooling internal body tissue. Blood moving through blood vessels in a cooled portion of the body is also cooled, and distribution of that cooled blood to other parts of the body thereby contributes to cooling other parts of the body.

Quick inducement of hypothermia requires that the patient's body temperature be rapidly reduced to the desired level, and involves a high rate of transfer of heat from the body. Impediments to inducing hypothermia include the patient's thermoregulatory responses to cooling. Shivering is a common thermoregulatory response that, in some cases, can increase body heat production to as much as 600% above basal levels. Anti-shivering drugs, and particularly meperidine, have been administered prior to or during active cooling to help suppress the shivering response. Such pharmacological treatment to suppress shivering is often successful, resulting in more rapid lowering of the patient's body temperature, to more quickly induce a desired degree of hypothermia. Some patients however, do not respond well to anti-shivering treatments or, even with successful suppression of shivering, are still difficult to cool rapidly enough to quickly induce a desired degree of hypothermia.

SUMMARY OF THE INVENTION

The invention is based on a recognition by the inventors that quick inducement of therapeutic hypothermia is significantly aided by the use of aggressive heat transfer from the human patient combined with administration to the patient of a vasodilation drug at a time to promote vasodilation that corresponds with some or all of the aggressive heat transfer. The invention is especially preferred when the aggressive heat transfer is by exterior surface cooling. Aggressive heat transfer from the exterior body surface rapidly removes thermal energy from near-surface regions of the patient's body. The vasodilation drug promotes dilation of blood vessels in the near surface region and, consequently, increased flow of blood through those blood vessels to assist more rapid cooling of other areas of the body.

One common thermoregulatory response to body cooling, and especially in the case of exterior surface cooling of the body, is for blood vessels in peripheral regions of the body to constrict, reducing the flow of blood through those peripheral body regions. The reduced blood flow accompanying this vasoconstriction means that less blood is available to be cooled in near-surface, peripheral regions of the body, and consequently the blood is less effectively used as an internal heat transfer medium for cooling other parts of the body. Dilation of blood vessels, through use of the vasodilation drug, promotes an increase in blood flow to counteract the vasoconstriction thermoregulatory response. Recognizing that the vasodilation effect may last only a short time, the administration of the vasodilation drug is combined with aggressive heat transfer occurring proximate in time to the administration of the vasodilation drug, to take advantage of the vasodilation period to quickly cool the body to induce hypothermia. In a preferred implementation of the invention, an anti-shivering drug is also administered to suppress the shivering thermoregulatory response, and in a further enhancement an anti-emetic drug is also administered to reduce patient nausea, and particularly nausea that may result from use of the anti-shivering drug. These other drug administrations should also be proximate in time to the period of aggressive heat transfer and to coincide with the vasodilation effect.

In one aspect, the invention provides a method for rapid inducement of hypothermia in a human patient, in which method cooling of the patient involves transferring, during a time of two hours or less, a quantity of heat larger than 200 kilocalories from the patient's body, and during that time there is a period of at least 20 minutes (and preferably significantly longer than 20 minutes) of very high heat transfer rate from the body to a heat exchange device in heat transfer communication with the body, such that the heat transfer rate from the body to the heat exchange device is larger than 250 kilocalories per hour, at least for that period. The method also involves administering a vasodilation drug to the patient to dilate blood vessels in the patient, and at least a portion of the administering of the vasodilation drug occurs between 30 minutes prior to the beginning of the noted period and the end of the noted period of very high heat transfer rate. Other portions of the vasodilation drug administered to the patient may be administered before 30 minutes prior to the beginning of the period and/or may be administered after the end of the period. Refinements for various implementations of this method are discussed below.

In other aspects, the invention involves use of the vasodilation drug in the method, including all of the various implementations of the method, and manufacture or preparation of the vasodilation drug for such use.

DETAILED DESCRIPTION OF PREFERRED EMBODIMENTS

Figure 1:
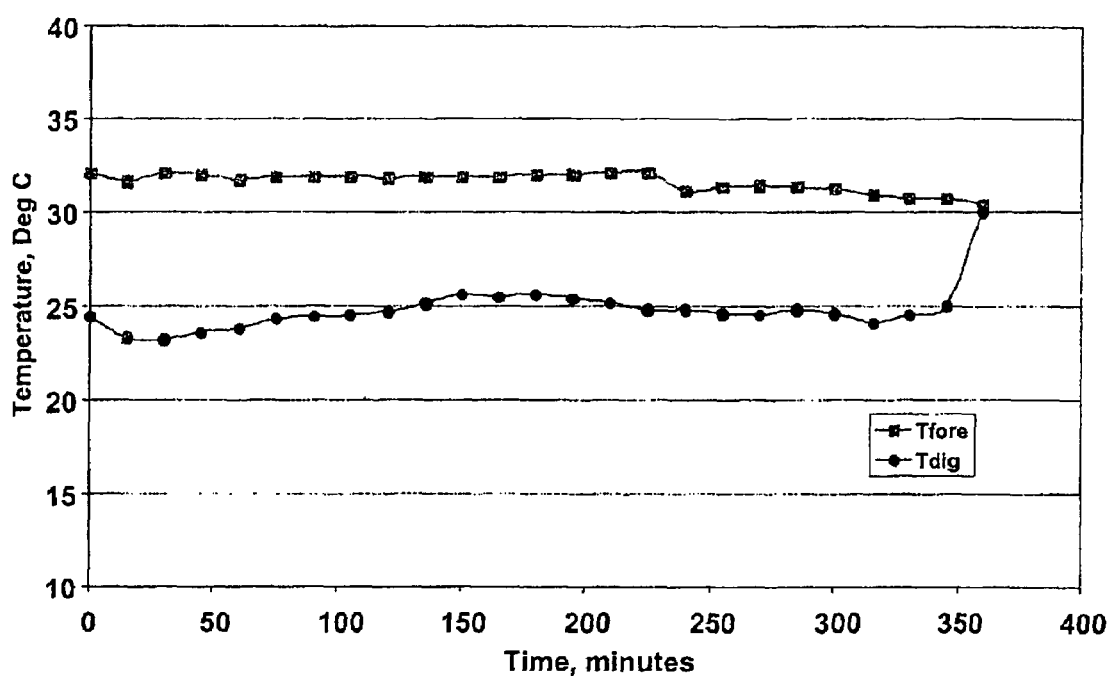
FIG. 1 is a plot over time of forearm temperature (Tfore) and fingertip temperature (Tdig) for subject #18 during Phase 3a testing discussed in the Examples section.

The cooling of the patient to lower the temperature of the body involves transferring heat from the patient's body. This heat transfer may be accomplished using any cooling equipment and techniques, or any combination of such equipment and techniques, including for example, the use of forced air cooling, contact cooling pads and/or the use of endovascular cooling devices and techniques.

In one implementation, the heat transfer may be accomplished with the use of a heat transfer fluid at a temperature that is lower than the body temperature of the patient. Air has a low heat capacity, and it is more difficult to achieve quick lowering of the body temperature using air or other gases as a heat transfer fluid, such as with forced air cooling. Liquids generally have higher heat capacities and are preferred for use as a heat transfer fluid.

To effect the heat transfer to cool the patient's body, the heat transfer fluid may be brought into heat transfer communication with the patient's body. With forced air cooling this could be accomplished for example by forcing the air to flow past at least a portion of the body to directly contact the body. A heat transfer liquid could also be directly contacted with a patient's body to effect a transfer of heat from the body, such as for example, by immersing a portion of the patient's body in a reservoir of the liquid.

Heat may also be transferred from the patient's body to a heat transfer fluid without direct contact between the fluid and the body. For example, the fluid may be contained within a heat transfer device (also referred to herein as a heat exchange device) that is in heat transfer communication with the body, such as through direct or indirect contact with an exterior surface of the body, such as contact with an exterior dermal surface. For example, when using a catheter heat transfer device located within the vasculature of the patient, a heat transfer liquid may be forced to flow through the device, with heat being conducted from the patient across one or more walls of the device and into the heat transfer fluid, which can be removed from the device to remove the heat from the vicinity of the patient, effecting the desired heat transfer and cooling.

In one preferred implementation of the invention, the heat transfer device is contacted with an exterior body surface. Establishing good heat transfer communication between the heat transfer device and the exterior body surface may be aided, for example, by the use of a gel, ointment or other medium between the heat transfer device and a dermal surface. A heat transfer fluid, preferably a liquid, may be circulated through the heat transfer device, wherein heat is conducted from the dermal surface, across one or more wall of the heat transfer device and into the heat transfer fluid. In one preferred refinement of the invention, the heat transfer device is in heat transfer communication with at least 0.3 square meter, preferably 0.4 square meter and more preferably 0.5 square meter of the exterior body surface, and the heat transfer device is in heat transfer communication with no more than 1.0 square meter, preferably 0.8 square meter and more preferably 0.7 square meter of the exterior body surface.

A contact pad is one preferred heat transfer device for cooling by contact with an exterior body surface. Preferably, the contact pad includes an adherent surface to achieve intimate contact with a patient's skin. Such an adherent surface may be provided by a thermally-conductive, hydrogel layer juxtaposed to a fluid circulation layer. In the latter regard, the fluid circulation layer may comprise fluid channels and dimples disposed to modify fluid flow characteristics for enhanced heat transfer performance. Examples of contact pads and their operation are disclosed in U.S. Pat. No. 6,197,045 entitled "COOLING/HEATING PAD AND SYSTEM", U.S. Pat. No. 6,375,674 entitled "COOLING/HEATING PAD AND SYSTEM", and U.S. patent application Ser. No. 10/087,533 having a filing date of Feb. 27, 2002, entitled "IMPROVED MEDICAL THERMAL ENERGY EXCHANGE PAD", the entire contents of each of which are incorporated by reference herein as if set forth herein in full. One example of a heat transfer system using one or more contact pad(s) is described below.

The system includes at least one heat exchanger to effect cooling of a fluid and a circulating pump for circulating the fluid through the heat exchanger and one or more interconnectable contact pad(s). Preferably, circulated fluid is drawn through the contact pad(s) under negative pressure. Such negative pressure may be established by locating the circulating pump downstream of the contact pad(s), wherein fluid is effectively pumped out of the contact pad(s) and then through the heat exchanger and back into the contact pad(s).

One or a plurality of fluid reservoirs may be located downstream of the heat exchanger. For example, a first fluid reservoir may be utilized to contain fluid that is removable therefrom to initially fill and then circulate through the contact pad(s). During normal heat exchange operations, fluid is circulatable through the contact pad(s) and the heat exchanger by the circulating pump substantially free from passage through the first fluid reservoir. The system may also comprise a second fluid reservoir through which fluid is circulated during normal heat exchange operations. By way of example, the first reservoir may be located to provide direct gravity fluid flow to the second reservoir. Further, the first reservoir may be vented to facilitate gas removal from the system.

In addition to the noted features, the system may further include various sensors to provide user feedback and automated control functionalities, thereby yielding enhanced patient thermal regulation. For example, the system may include a pressure sensor fluidly interconnected between an inlet side of the circulating pump and an outlet port of the interconnectable contact pad(s). Such pressure sensor may provide an output pressure signal employable (e.g. by a processor) to control the circulating pump (e.g. the flow rate therethrough) and thereby maintain negative pressure within the contact pad(s) within a predetermined range (e.g. thereby maintaining the desired flow rate through the contact pad(s)). Further, user alerts may be provided when the measured fluid pressure is within a predetermined range.

One or more fluid temperature sensors may also be utilized for sensing the temperature of the circulated fluid and providing an output temperature signal(s) in response thereto. The output temperature signal(s) may be utilized (e.g. by a processor) to control the operation of the heat exchanger. For example, the fluid output temperature signal(s) may be utilized to adjust the fluid temperature to within a predetermined range (e.g. as preset by a user). In this regard, patient temperature may also be monitored, wherein a patient temperature signal and the sensor output temperature signal(s) may be employed in combination to adjust the circulated fluid temperature. As may be appreciated, such temperature control functionality may be advantageously employed with the vasodilation drugs, and the optional anti-shivering and anti-emetic drugs, in accordance with present invention.

The above-noted system features and additional system functionalities may be incorporated as disclosed in U.S. patent application Ser. No. 09/976,197, having a filing date of Oct. 11, 2001, entitled "PATIENT TEMPERATURE CONTROL SYSTEM WITH FLUID TEMPERATURE RESPONSE", and U.S. patent application Ser. No. 10/233,843, having a filing date Sep. 3, 2002, entitled "PATIENT TEMPERATURE CONTROL SYSTEM WITH FLUID TEMPERATURE RESPONSE", the entire contents of each of which are hereby incorporated by reference as if set forth in full hereinbelow.

The degree by which a patient's body temperature is to be lowered will affect the amount of cooling that is used. In some implementations, the patient's body will be lowered by at least 0.5° C., in other implementations by at least 1° C. and by yet other implementations by at least 2° C. In most situations, the body temperature will be lowered by no more than 5° C. When reference is made to a person's body temperature, the reference is to the core temperature of the person, not the temperature of extremities. An indication of the core temperature is determinable, for example by measuring the temperature at a person's tympanic membrane, in a person's rectum or in a person's bladder. The degree by which a person's core temperature is lowered is determinable, for example, by monitoring temperature changes at the tympanic membrane, in the rectum or in the bladder.

In one embodiment of the invention, during a time of two hours or less, a quantity of heat larger than 200 kilocalories is transferred from the patient's body to a heat exchange device in heat transfer communication with the body. Preferably the quantity of heat is larger than 250 kilocalories and more preferably larger than 300 kilocalories. During this time, the core body temperature of the patient is typically reduced by at least 0.5° C., preferably by at least 1.0° C., and more preferably by at least 1.5° C. Moreover, within this time, there is a period of at least 20 minutes of very high heat transfer rate, over which period the heat transfer rate is larger than 250 kilocalories per hour. Preferably the heat transfer rate over this period is larger than 300 kilocalories per hour and more preferably larger than 350 kilocalories per hour. By heat transfer communication it is meant that the heat exchange device has a heat transfer surface in contact (directly or indirectly) with at least a portion of the body, such that heat can be transferred by conduction across the surface to remove heat from the body for transfer to the heat exchange device.

Furthermore, for enhanced effect according to the invention, vasodilation caused by administration of the vasodilation drug, and preferably also shivering suppression caused by administration of an anti-shivering drug (when used), should coincide with at least a portion of the above-noted time. Preferably, the vasodilation, and preferably also the shivering suppression should coincide with the period of very high heat transfer rate, which usually follows immediately after commencement of cooling of the patient's body with the heat exchange device. Therefore, at least a portion of the administration of the vasodilation drug should occur between 30 minutes prior to commencement of the period of very high heat transfer rate and the end of that period. Preferably, an entire loading dose of the vasodilation drug is administered between 30 minutes prior to commencement of the period of very high heat transfer rate and the end of that period, and more preferably administration of the loading dose of the vasodilation drug commences within 10 minutes before commencement of the very high heat transfer rate and is completed during that period. Even more preferably, administration of the loading dose takes from 10 to 45 minutes to complete. Particularly preferred is for the administration of the vasodilation drug to be timed so that during at least a portion of the period of very high heat transfer rate, the patient experiences vasodilation, which condition is indicated by the temperature of the patient's forearm being lower than the temperature of the patients fingertips.

When either or both of an anti-shivering drug and an anti-emetic drug are used, administration of at least a portion of each such drug that is used should likewise be administered between 30 minutes prior to the commencement of the period of very high heat transfer rate and the end of that period, and preferably a loading dose of each such drug that is used is completed prior to commencement of the period of very high heat transfer rate. When an anti-emetic drug is used, it is preferred that a loading dose of that drug be completed prior to commencing administration of either of the anti-shivering drug or the vasodilation drug.

In one preferred embodiment of the invention, the heat exchange device is in heat transfer communication with exterior surface of the patient's body, and heat transfer from the patient's body is across such exterior surface to the heat exchange device. This would be the case, for example, in the case of contact-cooling pads, with the area for heat transfer from the body to the heat transfer device being the area of the cooling pad surfaces that are brought into contact, directly or indirectly, with the exterior body surface. In the case of exterior body surface cooling, the heat transfer should be at a high flux across the heat transfer area. During the period of very high heat transfer rate discussed above, the cumulative heat transfer flux across the exterior body surface to the heat transfer device should be larger than 125 kilocalories per square meter of the exterior body surface that is in heat transfer communication with the heat exchange device, more preferably larger than 150 kilocalories per square meter and even more preferably larger than 200 kilocalories per square meter. Moreover, during the time for transferring the quantity of heat discussed above, the cumulative heat transfer flux across the exterior body surface to the heat exchange device should be larger than 500 kilocalories per square meter of the exterior body surface in heat transfer communication with the heat exchange device, and more preferably larger than 600 kilocalories per square meter. By heat transfer flux, or simply flux, it means the quantity of heat transferred per unit area of heat transfer surface per unit time. By cumulative heat transfer flux, or cumulative flux, it is meant the total quantity of heat transferred per unit area of heat transfer surface over a given period of time.

The vasodilation drug, and the anti-shivering drug and anti-emetic drug when used, should each be administered in a therapeutically effective quantity. By "therapeutically effective quantity" or "effective quantity" of a drug, it is meant that the drug at issue is administered at a dose and with a dosing regimen that is pharmacologically acceptable to treat for the target condition under the circumstances. As will be appreciated, different people will have varying responses to a "therapeutically effective quantity" of a drug.

The vasodilation drug (which may also be referred to as a vasodilator drug) may comprise one or more substances effective for dilating blood vessels, and preferably for dilating peripheral blood vessels close to the exterior body surface when cooling is accomplished by heat transfer across the exterior body surface. A variety of such vasodilation drugs are known or may be identified in the future. Examples of some vasodilation drugs include nitroprusside (e.g., in the form of sodium nitroprusside, such as in the NIPRIDE™ product) nitroglycerin, niacin and magnesium (e.g., in the form of a magnesium salt such as magnesium chloride or magnesium sulfate). A preferred vasodilation drug is magnesium, with a preferred form for administration being magnesium sulfate, which is typically administered as an aqueous solution of the salt. Another preferred vasodilation drug is niacin.

An initial, or loading dose, of magnesium is administered proximate in time to the commencement of aggressive heat transfer from the patient, which typically commences at the very start of cooling a patient with the heat exchange device. The initial dose may be administered through IV, preferably over a 15-20 minute period commencing within 10 minutes prior to commencement of such cooling. Preferably, a maintenance dose of the vasodilation drug is administered following the loading dose, such as for example by continuous infusion. The loading dose should be in a therapeutically effective quantity for dilating the desired blood vessels, and the maintenance dose should be administered at a sufficiently high rate to prolong the vasodilation condition during the cooling of the patient.

In one enhanced implementation of the invention, in addition to the vasodilation drug, an anti-shivering drug is also administered to the patient to suppress shivering response during the cooling of the patient. The anti-shivering drug is administered in a therapeutically effective quantity for suppression of shivering during some or all of the cooling of the patient's body. In a preferred variation of this implementation, an anti-emetic drug is also administered to the patient to reduce the potential for nausea that may be associated with use of the anti-shivering drug. The anti-emetic drug is administered in a therapeutically effective quantity to treat for the nausea.

To provide the suppression of shivering while the patient's body temperature is being lowered or while the temperature is in a lowered state, at least a portion of the anti-emetic drug and at least a portion of the anti-shivering drug should be administered prior to commencing the transfer of heat from the body to cool the body and/or while the transfer of heat from the body is being performed during cooling of the body. The method of administration may be by any suitable administration technique, such as, for example intravenous injection, continuous infusion or oral administration. One convenient technique is by intravenous injection as needed.

The anti-emetic drug and the anti-shivering drug may each be administered separately. Each of the anti-emetic drug and the anti-shivering drug may be administered as a single dose, or using a multiple dose regimen involving an initial dose followed by one or more successive, and usually smaller, doses. For the anti-shivering drug, a multiple dose regimen may involve an initial dose to commence the shivering suppression followed by successive doses being administered as required to maintain the shivering suppression. The timing for subsequent dose administrations may be determined, for example by visual observation of the patient for indications that an onset of shivering is approaching. For the anti-emetic drug, a single dose given prior to or soon after commencement of active cooling may be sufficient, although a multiple dose regimen may be better when it is anticipated that cooling and body temperature suppression may extend for a significant duration. For example, an initial dose of the anti-emetic drug may be followed later by one or more supplemental doses as appropriate based on the pharmacokinetic properties of the specific anti-emetic drug. In one preferred implementation, at least a portion of the anti-emetic drug is administered to the patient prior to commencement of the cooling heat transfer, and also preferably prior to administration of any of the anti-shivering drug.

The anti-shivering drug may comprise one or more substance effective for suppressing shivering. A variety of such anti-shivering drugs are known or may be identified in the future. Examples of some reported anti-shivering drugs include certain non-opioid analgesics (for example, tramodol and nefopan), certain opioid analgesics (for example, alfentanil, morphine, fentanyl, meperidine, naloxone and nalbuphine), certain $\alpha_2$-andrenergic agonists (for example, clonidine and dexmedetomidine) and certain serotonin antagonists (for example, ketanserin and ondansetron). Also, multiple anti-shivering drugs may be used to the extent that they are pharmacologically compatible. Moreover, it should be appreciated that drugs are often administered in the form of pharmacologically acceptable salts, so, for example, the anti-shivering drug may be such a salt of any of the foregoing listed compounds. Meperidine, or a salt thereof, is particularly preferred for use as the anti-shivering drug. Unless otherwise required by the specific context, when a reference is made herein, including in the claims, to a drug compound, the reference includes the named compound and chemical variations of the named compound, and particularly includes salts of the compound, that are pharmacologically acceptable for administration to human subjects.

The anti-emetic drug is different than the anti-shivering drug, and the anti-emetic drug may comprise one or more substance effective for suppressing nausea and/or vomiting. A variety of such anti-emetic drugs are known or may be identified in the future. Examples of some anti-emetic drugs include certain $D_2$ dopamine antagonists/blocking agents (for example, phenothiazine antipsycotics such as prochlorperazine, triflupromazine, chlorpromazine and trifluorperazine; and metoclopramide), promethazine (both a $D_2$ dopamine antagonist and an $H_1$ histamine antagonist), certain antihistamines with anticholinergic effects (for example, diphenhydramine, dimenhydrinate and meclizine), and certain serotonin antagonists (for example, ondansetron, granisetron and tropisetron, which are 5-$HT_3$ antagonists). Preferred for use as the anti-emetic drug is one or more 5-$HT_3$ antagonist. Also, multiple anti-emetic drugs may be used to the extent they are pharmacologically compatible. Moreover, as noted above, drugs are often administered in the form of pharmacologically acceptable salts, so for example, the anti-emetic drug may be such a salt of any of the foregoing listed compounds. Ondansetron, or a salt thereof, is particularly preferred for use as the anti-emetic drug.

In one preferred implementation of the invention, the anti-emetic drug comprises a 5-$HT_3$ antagonist and the anti-shivering drug comprises an opioid analgesic. A particularly preferred pairing is for the anti-emetic drug to comprise ondansetron, or a salt thereof, and the anti-shivering drug to comprise meperidine, or a salt thereof. In one particularly preferred implementation, the use of the anti-emetic drug in combination with the anti-shivering drug reduces the quantity of the anti-shivering drug required to treat for the shivering suppression, relative to use of the anti-shivering drug alone. For example, an anti-emetic drug can be selected that independently acts to provide at least some level of shivering suppression. This is the case, for example, with the use of ondansetron, which as noted above has been reported for shivering suppression.

EXAMPLES

Mild hypothermia is induced and maintained in healthy subjects for up to several hours. Table 1 summarizes data concerning the subjects for each phase of testing (Phases 1, 3a, 4, 5 and 6). Each volunteer is cooled using contact-cooling pads (Arctic Sun Energy Transfer Pads™, Medivance, Inc., Louisville, Colo., U.S.A.). Contact-cooling pads are applied to contact the subjects, and water at a controlled temperature is delivered to and circulated through the contact pads to effect the controlled cooling of each volunteer.

TABLE 1

Subject Characteristics

| Phase | Subject # | Age (yrs) | Sex | Weight (kg) | Height (cm) | BSA ($M^2$) |
|---|---|---|---|---|---|---|
| 1 | 1 | 35 | M | 66 | 173 | 1.79 |
|   | 2 | 40 | M | 91 | 183 | 2.13 |
|   | 3 | 41 | F | 61 | 165 | 1.67 |
|   | 4 | 36 | M | 91 | 183 | 2.13 |
|   | 5 | 29 | F | 68 | 185 | 1.90 |
|   | Mean ± SD | 36 ± 5 |   | 75 ± 15 | 178 ± 13 | 1.92 ± 0.2 |
| 3a | 18 | 21 | F | 48 | 163 | 1.50 |
|   | 19 | 22 | M | 98 | 193 | 2.29 |
|   | 20 | 33 | F | 65 | 161 | 1.69 |
|   | 22 | 25 | F | 48 | 164 | 1.50 |
|   | 23 | 48 | F | 67 | 170 | 1.78 |

TABLE 1-continued

Subject Characteristics

| Phase | Subject # | Age (yrs) | Sex | Weight (kg) | Height (cm) | BSA (M$^2$) |
|---|---|---|---|---|---|---|
|   | Mean ± SD | 30 ± 11 |   | 65 ± 20 | 170 ± 13 | 1.75 ± 0.3 |
| 4 | 24 | 26 | F | 64 | 152 | 1.61 |
|   | 25 | 39 | F | 74 | 157 | 1.75 |
|   | 26 | 19 | M | 73 | 178 | 1.90 |
|   | 27 | 26 | M | 64 | 165 | 1.70 |
|   | Mean ± SD | 28 ± 8 |   | 69 ± 6 | 163 ± 11 | 1.74 ± 0.1 |
| 5 | 29 | 37 | F | 51 | 168 | 1.57 |
|   | 31 | 30 | M | 84 | 178 | 2.03 |
|   | 32 | 35 | M | 71 | 178 | 1.88 |
|   | 33 | 20 | F | 61 | 168 | 1.69 |
|   | 34 | 35 | M | 139 | 183 | 2.56 |
|   | 35 | 42 | F | 65 | 171 | 1.76 |
|   | Mean ± SD | 33 ± 8 |   | 79 ± 32 | 174 ± 6 | 1.92 ± 0.4 |
| 6 | 37 | 39 | M | 91 | 183 | 2.13 |
|   | 38 | 27 | F | 80 | 168 | 1.90 |
|   | 39 | 40 | F | 95 | 170 | 2.06 |
|   | 40 | 38 | M | 109 | 185 | 2.32 |
|   | 41 | 23 | F | 57 | 168 | 1.64 |
|   | 42 | 32 | M | 93 | 185 | 2.17 |
|   | 43 | 42 | F | 95 | 170 | 2.06 |
|   | 44 | 20 | F | 64 | 160 | 1.67 |
|   | Mean ± SD | 33 ± 8 |   | 86 ± 17 | 174 ± 9 | 1.99 ± 0.2 |

BSA = body surface area

Phase 1

Four contact pads are applied to the thighs and chest of each subject and each subject is rapidly cooled with an objective of reducing core body temperature to 34-35° C. Core body temperatures are measured at the tympanic membrane and the rectum. Mean skin-surface temperature is determined from the weighted average of calf, thigh, chest, and upper arm skin temperatures. Thermoregulatory vasoconstriction is evaluated using forearm minus fingertip skin-temperature gradients. Temperatures are measured using Mon-a-Therm™ themocouple probes connected to Mallinckrodt Model 6510 two-channel electronic thermometers having an accuracy near 0.1° C. (Mallinckrodt Anesthesia Products, St. Louis, Mo., U.S.A.). Temperatures are recorded before cooling is started (i.e., baseline) and subsequently at 15-minute intervals.

Each of subjects 1-5 is administered a single dose of acetomiophen (1000 mg) within 20 minutes prior to treatment and is administered a bolus of intravenous (IV) meperidine (Demerol®, 25-75 mg) within 5 minutes of the start of cooling. Subjects also receive initial doses of chlorpromazine (Thorazine®, 12.5-25 mg, IV). Active cooling is initiated and the inlet water temperature is controlled to achieve a target tympanic temperature between 34° C. and 35° C. Additional doses of meperidine and/or chlorpromazine are administered to maintain comfort and to prevent shivering. Active cooling and maintenance of hypothermia continues for up to five hours, after which subjects are actively re-warmed to tympanic and rectal temperatures of at least 36° C.

The presence of shivering is noted by physical examination, electromyographic artifact on continuous electrocardiography (ECG), or by subject report. Overall thermal comfort is evaluated at 15-min intervals with a 100-mm-long visual analog scale (VAS) on which 0 mm defines the worst imaginable cold, 50 mm identifies thermal neutrality, and 100 mm indicates unbearable heat. A new, unmarked scale is used for each assessment. Heart rate and oxyhemoglobin saturation are monitored using ECG and pulse oximetry; arterial blood pressure is recorded oscillometrically at 15-minute intervals.

Phase 3a

Five contact-cooling pads are applied to the thighs, back and abdomen of each subjects, and actively cooled. The pads cover and contact about 0.6 square meter of the subject's exterior body surface area, which is the area in heat transfer communication between the pads and the subject's body. Temperatures are measured in the same manner as in Phase 1 except that the rectal temperature probe is connected to a control module and the rectal temperature signal is used by the control module to adjust inlet water temperature via a feedback control algorithm to achieve a target core body temperature of 34.5° C.

A single oral dose of acetaminophen (1000 mg), is administered within 20 minutes prior to treatment. A bolus of IV meperidine (Demerol®, 50-100 mg) is given within 5 minutes of the start of active cooling. Additional doses of meperidine are administered to maintain comfort and to prevent shivering. Active cooling and maintenance of hypothermia continues for five hours. As in the Phase 1, the subjects are actively re-warmed to a tympanic and rectal temperatures of at least of 36° C. prior to termination of the experiment. Shivering, comfort, oxyhemoglobin saturation, and arterial blood pressure are recorded as in Phase 1.

Table 2 summarizes results for Phase 1 and Phase 3a. Results are expressed as mean ±SD. Five subjects are enrolled in Phase 1. Subject characteristics are summarized in Table 1. Mild hypothermia is attained in all subjects. The mean time to reach a tympanic temperature of 35° C. is 77±23 minutes which corresponds to a mean cooling rate of 1.5±0.6° C./hr. Details of the cooling responses of the individual subjects are presented in Table 2. The mean total dosage of merperidine is 280±155 mg. Only subjects #1 (37.5 mg) and #2 (12.5 mg) received chloropromazine.

TABLE 2

Cooling Response of Subjects, Phases 1 & 3a

| Phase | Subject # | $T_{initial}$ (° C.) | Time to 35° C. (min) | Cooling rate to 35° C. (° C./hr) | Total Meperidine Dose (mg) | Nausea or Vomiting During Treatment |
|---|---|---|---|---|---|---|
| 1 | 1 | 36.8 | 41 | 2.6 | 75 | None |
| | 2 | 36.6 | 82 | 1.2 | 200 | None |
| | 3 | 36.9 | 81 | 1.4 | 275 | Pruritis |
| | 4 | 36.7 | 105 | 1.0 | 375 | None |
| | 5 | 37.0 | 78 | 1.5 | 475 | None |
| | Mean ± SD | 36.8 ± .2 | 77 ± 23 | 1.5 ± .6 | 280 ± 155 | |
| 3a | 18 | 37.0 | 64 | 1.9 | 400 | Nausea end |
| | 19 | 37.7 | 180 | .9 | 500 | None |
| | 20 | 36.9 | 94 | 1.2 | 350 | Nausea end |
| | 22 | 36.8 | 56 | 1.9 | 350 | Nausea early, end |
| | 23 | 36.6 | 46 | 2.1 | 250 | Nausea, vomiting mid |
| | Mean ± SD | 37.0 ± .4 | 88 ± 54 | 1.6 ± 0.5 | 370 ± 91 | |

T = tympanic membrane temperature

Six subjects are enrolled in the Phase 3a. One subject is withdrawn from the study prior to the initiation of cooling due to vasovagal syncope at the time of IV insertion. Subject characteristics of the remaining 5 subjects are presented in Table 1. Details of the cooling responses of the subjects are presented in Table 2.

In all subjects, there is no statistically significant change in heart rate, diastolic blood pressure, or blood oxygenation compared with baseline. Systolic blood pressure is significantly elevated compared with baseline only for the 180 min timepoint (140±20 vs 122±13 mm Hg; p=0.042). The mean total meperidine dosage in Phase 3a is 90mg higher than in Phase 1 (370 mg vs 280 mg; p=0.28, t-test). Comfort is statistically significantly lower than baseline for all timepoints during active cooling (except T=135min) although no subject requested that the study be terminated.

In Phases 1 and 3a, meperidine is used to suppress shivering and to maintain comfort. Although no respiratory compromise is observed, nausea is observed in 30% of subjects. All cases of nausea occurred in Phase 3a making the trend toward a higher total meperidine dosage in Phase 3a noteworthy.

Phase 4

Phase 4 proceeds as described for Phase 3a, except as noted. In addition to meperidine (Demerol®), subjects are also given an oral dose of 30-60 mg buspirone. Subject characteristics are summarized in Table 1. Results are summarized in Table 3.

Five subjects are enrolled in Phase 4. One subject is withdrawn due to sustained nausea and vomiting throughout the treatment period. Details of the cooling responses of the individual subjects are presented in Table 3. As seen in Table 3, the use of buspirone did not reduce the incidence of nausea in those four subjects.

TABLE 3

Cooling Response of Subjects, Phase 4

| Phase | Subject # | $T_{initial}$ (° C.) | Time to 35° C. (min) | Cooling rate to 35° C. (° C./hr) | Total Meperidine Dose (mg) | Nausea or Vomiting During Treatment |
|---|---|---|---|---|---|---|
| 4 | 24 | 36.9 | 63 | 1.8 | 250 | Nausea mid |
| | 25 | 37.3 | 158 | 0.9 | 400 | Nausea end |
| | 26 | 37.0 | 120 | 1.0 | 250 | Nausea early, Vomiting end |
| | 27 | 36.8 | 95 | 1.1 | 250 | None |
| | Mean ± SD | 37.0 ± .2 | 109 ± 40 | 1.2 ± 0.4 | 288 ± 75 | |

T = tympanic membrane temperature

Phase 5

Phase 5 Phase 5 proceeds as described for Phase 3a, except as noted. The temperature of water circulated to the contact-cooling pads is controlled to achieve a target core body temperature of 34.5° C. In addition to meperidine (Demerol®), subjects are also given an IV dose of 8 mg ondansetron (hydrochloride salt, Glaxo Wellcome). Subject characteristics are summarized in Table 1. Results are summarized in Table 4.

Five subjects are initially enrolled in Phase 5, and two subjects are later added to bring the total to seven subjects. One subject is withdrawn due to a mild allergic reaction to meperidine, which caused a facial rash. Mild hypothermia is attained in all subjects, the mean time to reach a tympanic temperature of 35.0° C. is 131±100 minutes, corresponding to a cooling rate of 1.3° C./hr. Details of the cooling responses of the individual subjects are presented in Table 4. The mean total dosage of meperidine is 271±77 mg.

Subject #29 feels very warm at the end of the treatment, and becomes nauseated and vomits immediately after the treatment. The nausea and vomiting is believed to be due to a fast rate of warming of the subject. The rate of warming is reduced for subsequent subjects, who do not become nauseated and do not vomit during the treatment. Thus, the use of ondansetron reduces the incidence of nausea and vomiting, relative to Phases 3a and 4. In addition, there is a trend toward less meperidine administration in Phase 5 relative to Phase 3a (p=0.26, t-test). Furthermore, the mean comfort score for the subjects is higher in Phase 5 than in Phases 1, 3a and 4.

Moreover, during a subsequent test conducted in a manner similar to that described for Phase 5, a subject is administered an initial dose of 8 mg of the ondansetron followed by a supplemental dose of 8 mg of the ondansetron administered 3.5 hours later. The subject does not experience nausea.

Phase 6

Phase 6 proceeds as described for Phase 5, except as noted. IV meperidine (Demerol®), ondansetron (hydrochloride salt, Glaxo Wellcome), and magnesium sulfate are given as loading doses within 5 minutes prior to commencement of body cooling, except that the magnesium sulfate loading dose is administered over a 15 minute period that extends into the early phase of cooling. Following administration of the loading dose, a maintenance dose of magnesium sulfate is given for the remainder of the treatment by continuous infusion. Supplemental IV meperidine is given as needed to suppress shivering. A supplemental IV dose of ondonsetron (4 mg) is given at approximately the midpoint of treatment. Subject characteristics are summarized in Table 1. Results are summarized in Table 5. Heat transfer data for Phase 5 and Phase 6 subjects are summarized in Table 6.

TABLE 4

Cooling Response of Subjects, Phase 5

| Phase | Subject # | $T_{initial}$ (° C.) | Time to 35° C. (min) | Cooling rate to 35° C. (° C./hr) | Total Meperidine Dose (mg) | Nausea or Vomiting During Treatment |
|---|---|---|---|---|---|---|
| 5 | 29 | 36.9 | 60 | 1.9 | 375 | Nausea and vomiting immediately post |
|   | 31 | 37.0 | 80 | 1.5 | 275 | None |
|   | 32 | 36.4 | 58 | 1.4 | 250 | None |
|   | 33 | 37.3 | 88 | 1.6 | 325 | Nausea post |
|   | 34 | 37.5 | 310 | 0.5 | 150 | None |
|   | 35 | 36.9 | 189 | 0.6 | 250 | Nausea post |
|   | Mean ± SD | 37.0 ± 0.4 | 131 ± 100 | 1.3 ± 0.6 | 271 ± 77 | |

T = tympanic membrane temperature

TABLE 5

Cooling Response of Subjects, Phase 6

| Phase | Subject # | $T_{initial}$ (° C.) | Time to 35° C. (min) | Cooling rate to 35° C. (° C./hr) | Total Meperidine Dose (mg) | Nausea or Vomiting During Treatment |
|---|---|---|---|---|---|---|
| 6 | 37 | 36.6 | 50 | 1.9 | 425 | None |
|   | 38 | 36.9 | 115 | 1.0 | 400 | None |
|   | 39 | 36.9 | 105 | 1.0 | 250 | None |
|   | 40 | 36.8 | 105 | 1.0 | 350 | None |
|   | 41 | 37.2 | 75 | 1.8 | 300 | None |
|   | 42 | 36.5 | 75 | 1.2 | 275 | None |
|   | 43 | 36.8 | 98 | 1.0 | 250 | None |
|   | 44 | 37.0 | 67 | 1.8 | 350 | Yes - early |
|   | Mean ± SD | 36.8 ± 0.2 | 86 ± 23 | 1.3 ± 0.4 | 325 ± 67 | |

T = tympanic membrane temperature

TABLE 6

Heat Transfer From Subjects, Phases 5 & 6

Cumulative Heat Transfer From Subject At Various Times After Initiation Of Cooling (Kcal)*

| Subject | 5 Min | 10 Min | 15 Min | 20 Min | 25 Min | 30 Min | 45 Min | 60 Min | 75 Min | 90 Min | 105 Min | 120 Min |
|---|---|---|---|---|---|---|---|---|---|---|---|---|
| 29 | 37.16 | 73.79 | 109.68 | 142.73 | 169.85 | 184.74 | 205.19 | 212.94 | 284.94 | 348.14 | 375.85 | 407.01 |
| 31 | 48.61 | 84.78 | 124.12 | 163.01 | 200.85 | 239.02 | 354.67 | 467.30 | 574.88 | 676.99 | 708.76 | 733.20 |
| 32 | 45.90 | 82.99 | 118.51 | 151.96 | 184.79 | 218.02 | 309.30 | 346.56 | 361.63 | 367.39 | 366.43 | 368.56 |
| 33 | 44.85 | 79.01 | 111.35 | 142.43 | 172.00 | 201.44 | 282.20 | 353.28 | 423.43 | 436.35 | 458.46 | 457.78 |
| 34 | 53.91 | 96.81 | 136.59 | 175.59 | 214.2 | 252.02 | 360.32 | 466.28 | 567.71 | 667.78 | 767.83 | 867.73 |
| 35 | — | — | — | — | — | — | — | — | — | — | — | — |
| 37 | 50.84 | 83.90 | 114.06 | 142.95 | 171.71 | 200.27 | 284.48 | 330.06 | 398.79 | 474.16 | 513.57 | 551.87 |
| 38 | 56.05 | 94.45 | 131.65 | 167.05 | 201.50 | 235.67 | 337.88 | 438.39 | 536.70 | 631.53 | 725.20 | 817.42 |
| 39 | 53.07 | 89.64 | 124.04 | 157.16 | 186.88 | 214.96 | 298.48 | 369.56 | 436.89 | 496.74 | 555.89 | 594.40 |
| 40 | 56.55 | 95.43 | 131.43 | 165.27 | 195.15 | 225.03 | 309.97 | 384.78 | 455.34 | 522.05 | 560.88 | 592.85 |
| 41 | 45.83 | 78.03 | 106.23 | 131.43 | 155.87 | 179.14 | 238.29 | 294.75 | 305.22 | 316.31 | 336.77 | 387.48 |
| 42 | 53.74 | 91.14 | 125.48 | 158.12 | 188.38 | 218.48 | 303.38 | 382.72 | 453.61 | 523.08 | 475.65 | 380.12 |
| 43 | — | — | — | — | — | — | — | — | — | — | — | — |
| 44 | — | — | — | — | — | — | — | — | — | — | — | — |

*Gross values based on temperature change in cooling liquid, not corrected for ambient warming through portions of contact-cooling pads not in contact with the subject's body. Corrected values are approximately 15% smaller.

Figure 2:
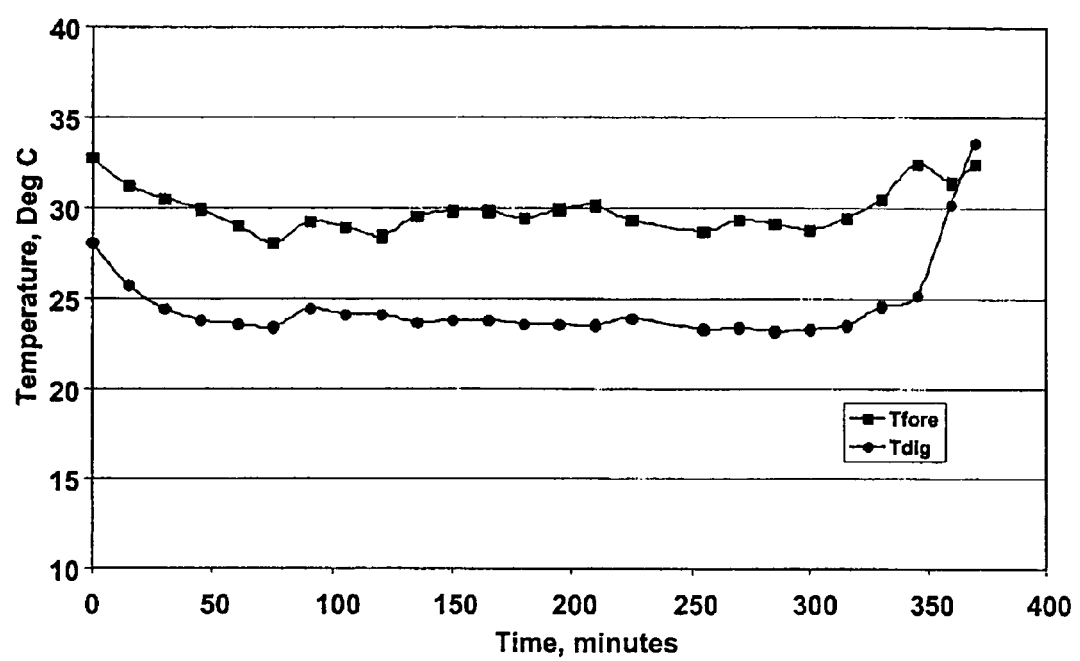
FIG. 2 is a plot over time of forearm temperature (Tfore) and fingertip temperature (Tdig) for subject #19 during Phase 3a testing discussed in the Examples section.
Figure 3:
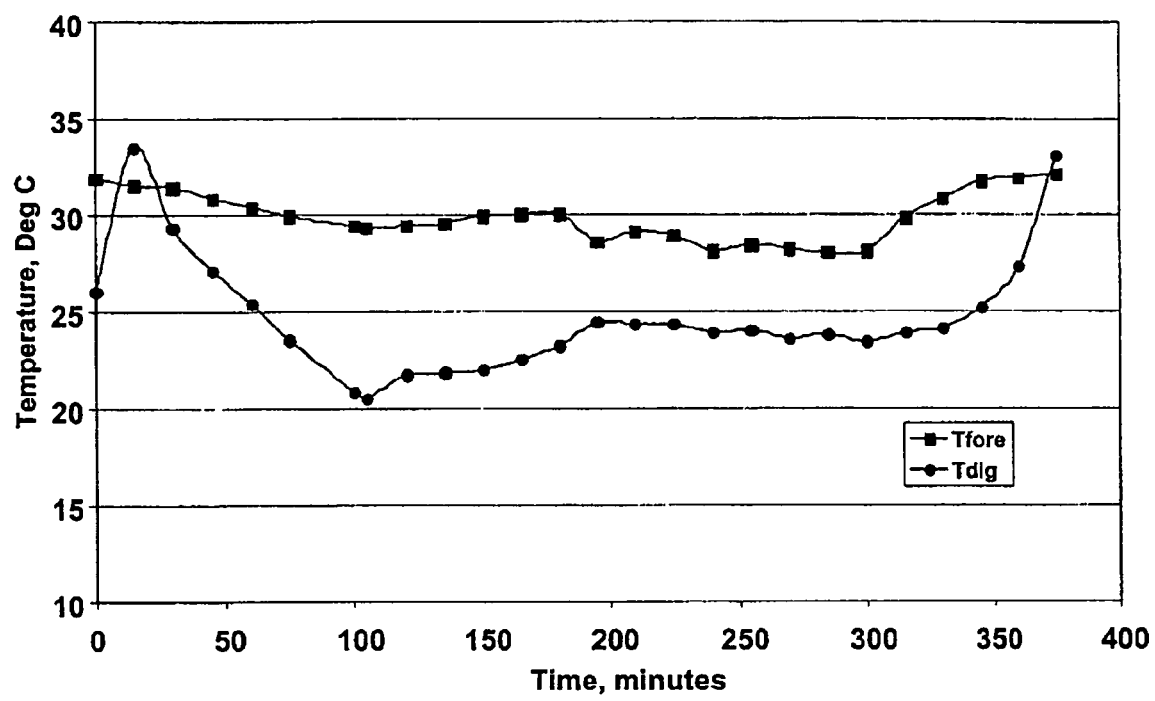
FIG. 3 is a plot over time of forearm temperature (Tfore) and fingertip temperature (Tdig) for subject #20 during Phase 3a testing discussed in the Examples section.
Figure 4:
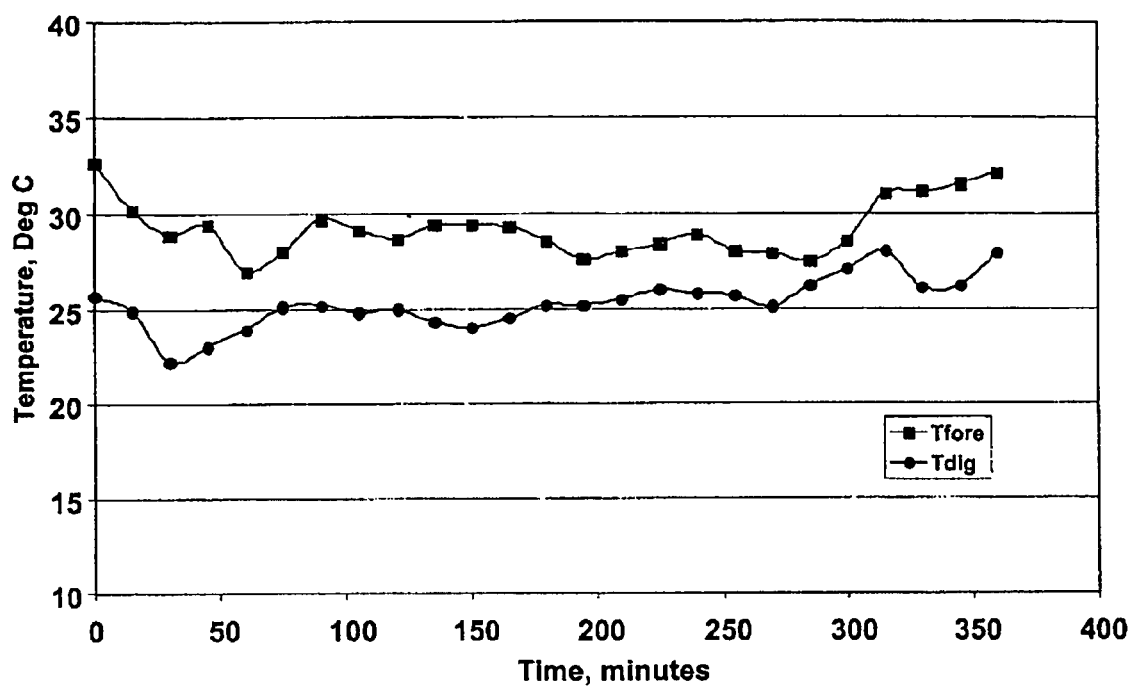
FIG. 4 is a plot over time of forearm temperature (Tfore) and fingertip temperature (Tdig) for subject #22 during Phase 3a testing discussed in the Examples section.
Figure 5:
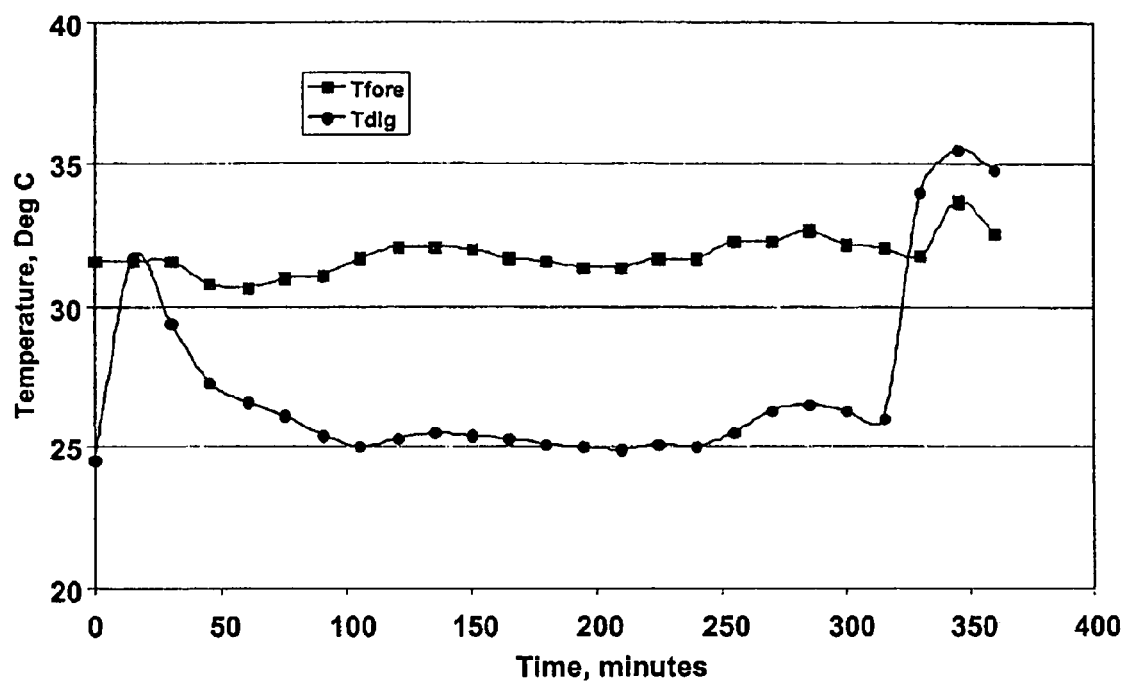
FIG. 5 is a plot over time of forearm temperature (Tfore) and fingertip temperature (Tdig) for subject #23 during Phase 3a testing discussed in the Examples section.
Figure 6:
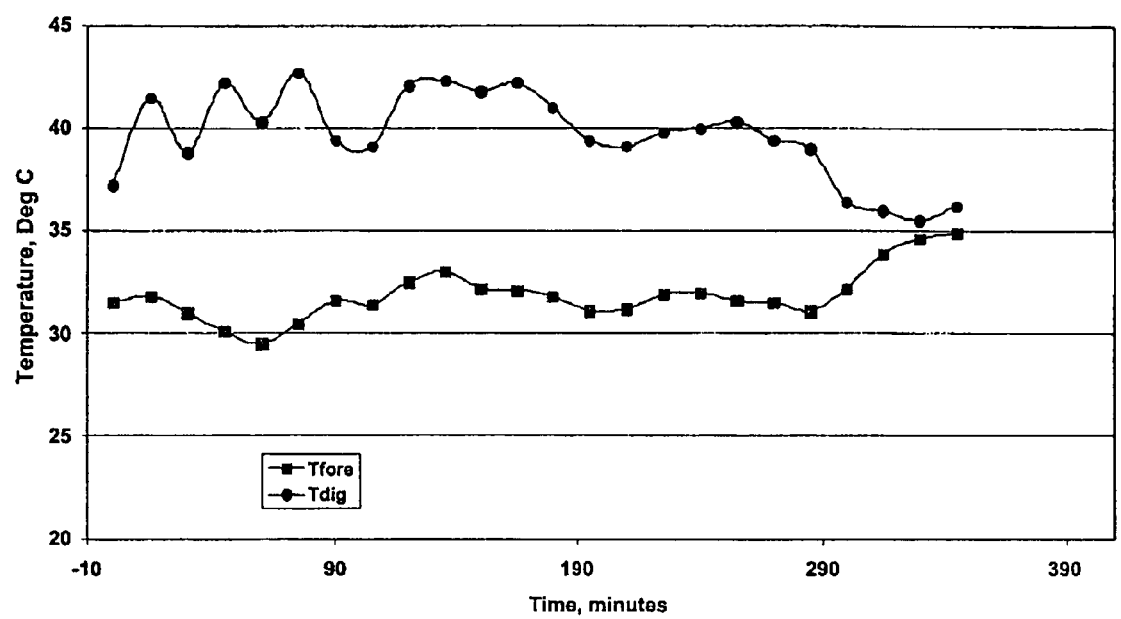
FIG. 6 is a plot over time of forearm temperature (Tfore) and fingertip temperature (Tdig) for subject #24 during Phase 4 testing discussed in the Examples section.
Figure 7:
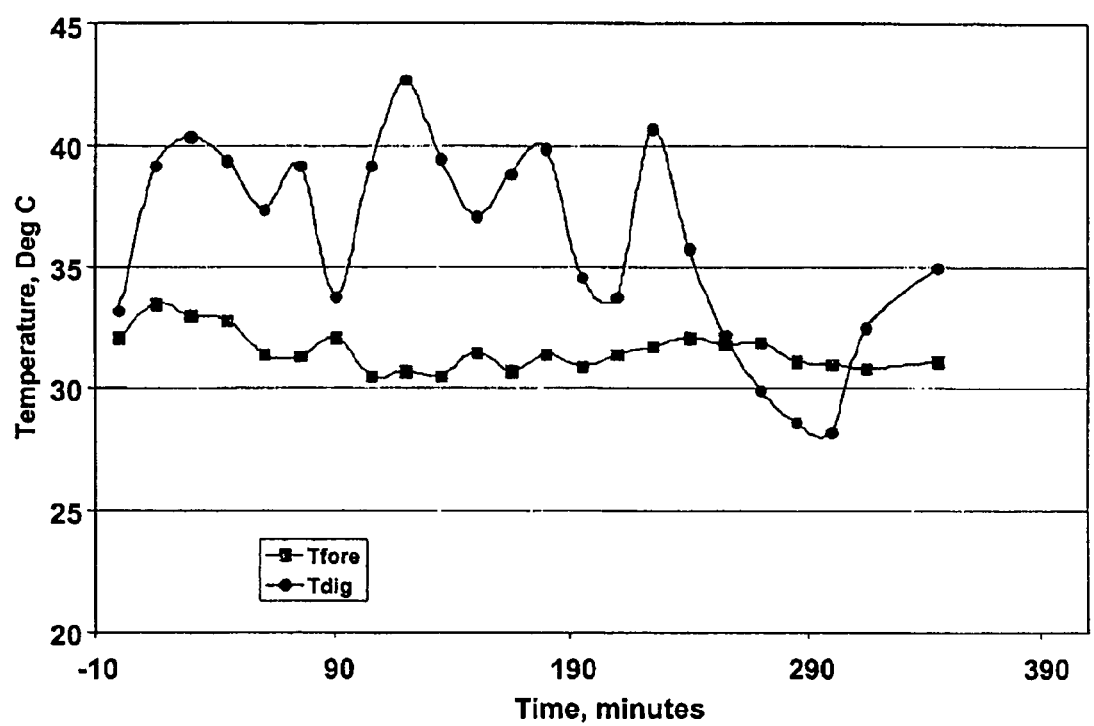
FIG. 7 is a plot over time of forearm temperature (Tfore) and fingertip temperature (Tdig) for subject #25 during Phase 4 testing discussed in the Examples section.
Figure 8:
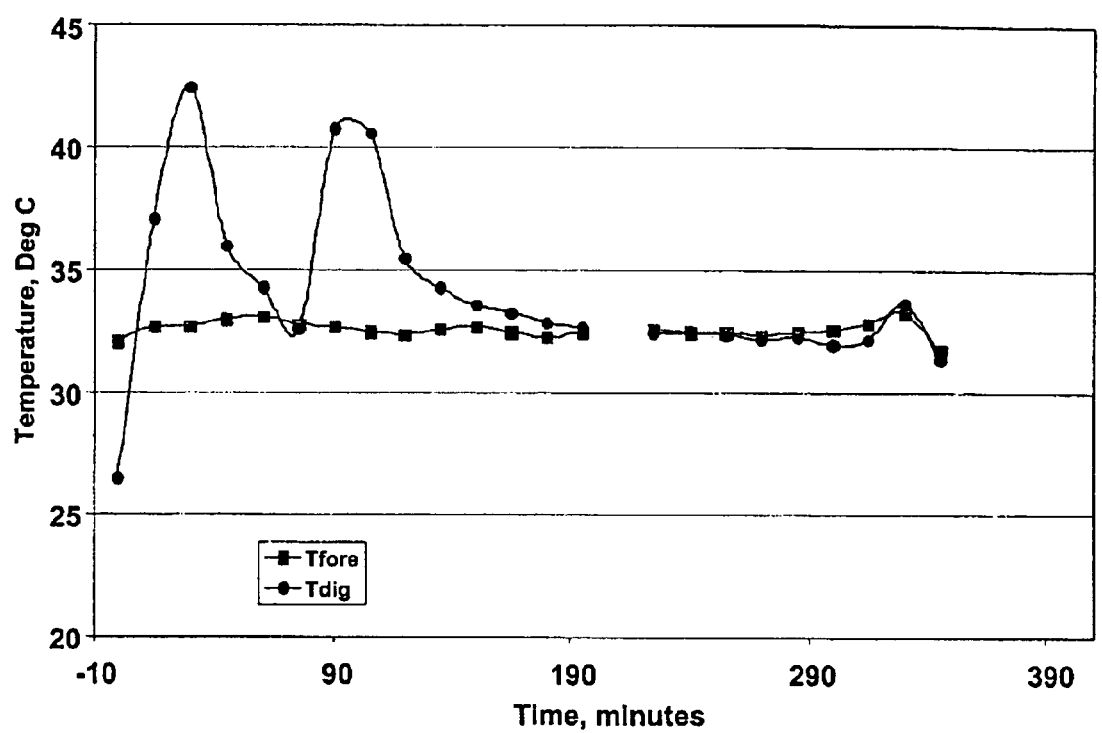
FIG. 8 is a plot over time of forearm temperature (Tfore) and fingertip temperature (Tdig) for subject #26 during Phase 4 testing discussed in the Examples section.
Figure 9:
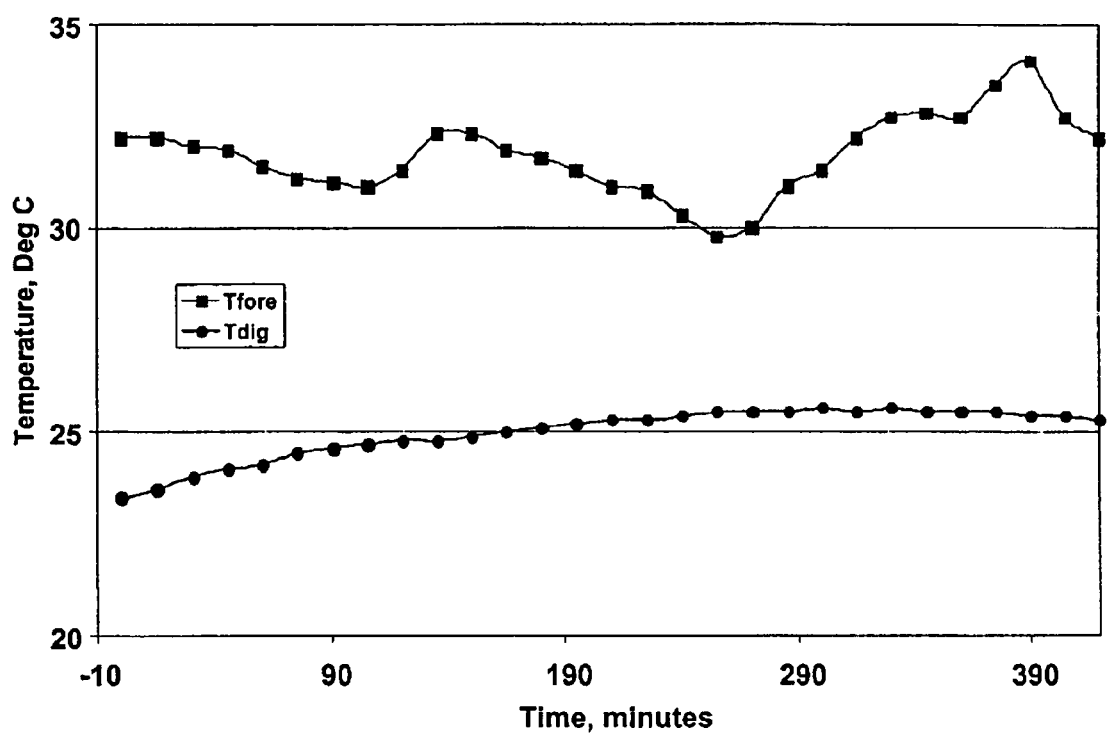
FIG. 9 is a plot over time of forearm temperature (Tfore) and fingertip temperature (Tdig) for subject #27 during Phase 4 testing discussed in the Examples section.
Figure 10:
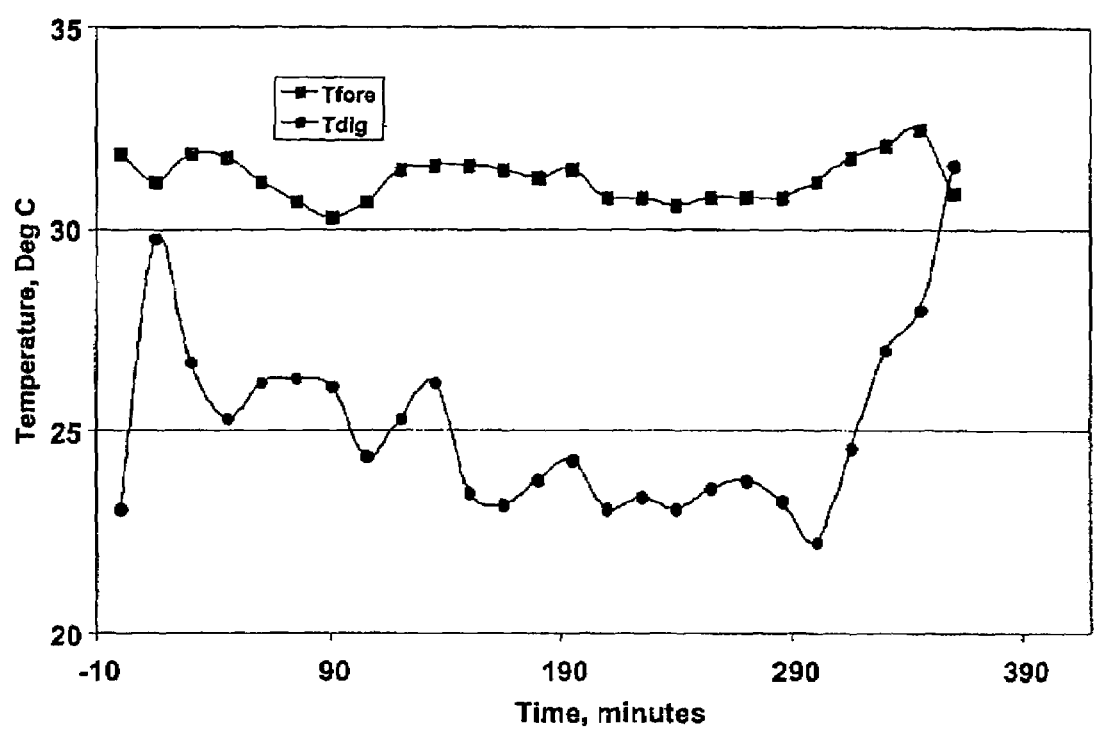
FIG. 10 is a plot over time of forearm temperature (Tfore) and fingertip temperature (Tdig) for subject #29 during Phase 5 testing discussed in the Examples section.
Figure 11:
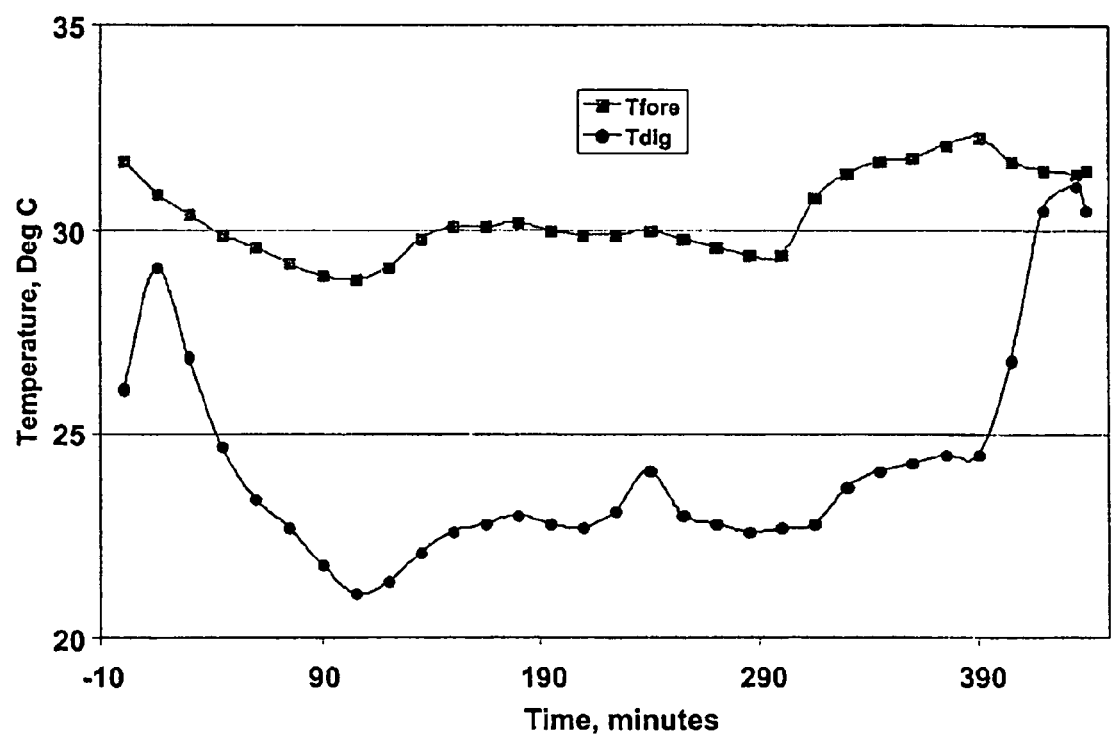
FIG. 11 is a plot over time of forearm temperature (Tfore) and fingertip temperature (Tdig) for subject #31 during Phase 5 testing discussed in the Examples section.
Figure 12:
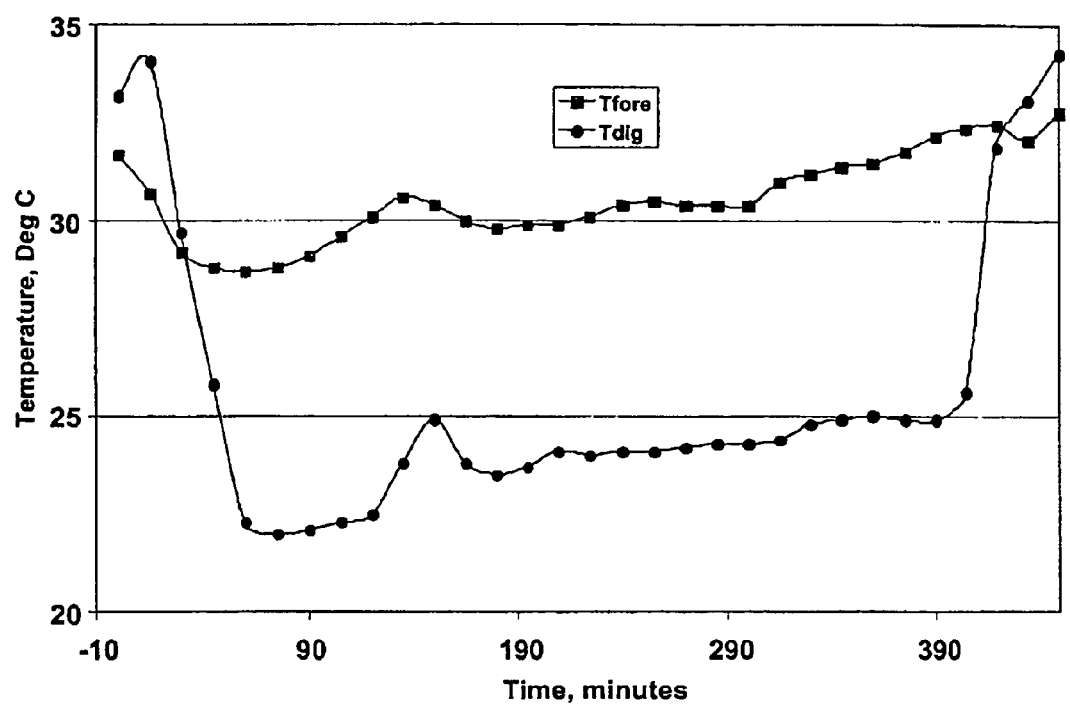
FIG. 12 is a plot over time of forearm temperature (Tfore) and fingertip temperature (Tdig) for subject #32 during Phase 5 testing discussed in the Examples section.
Figure 13:
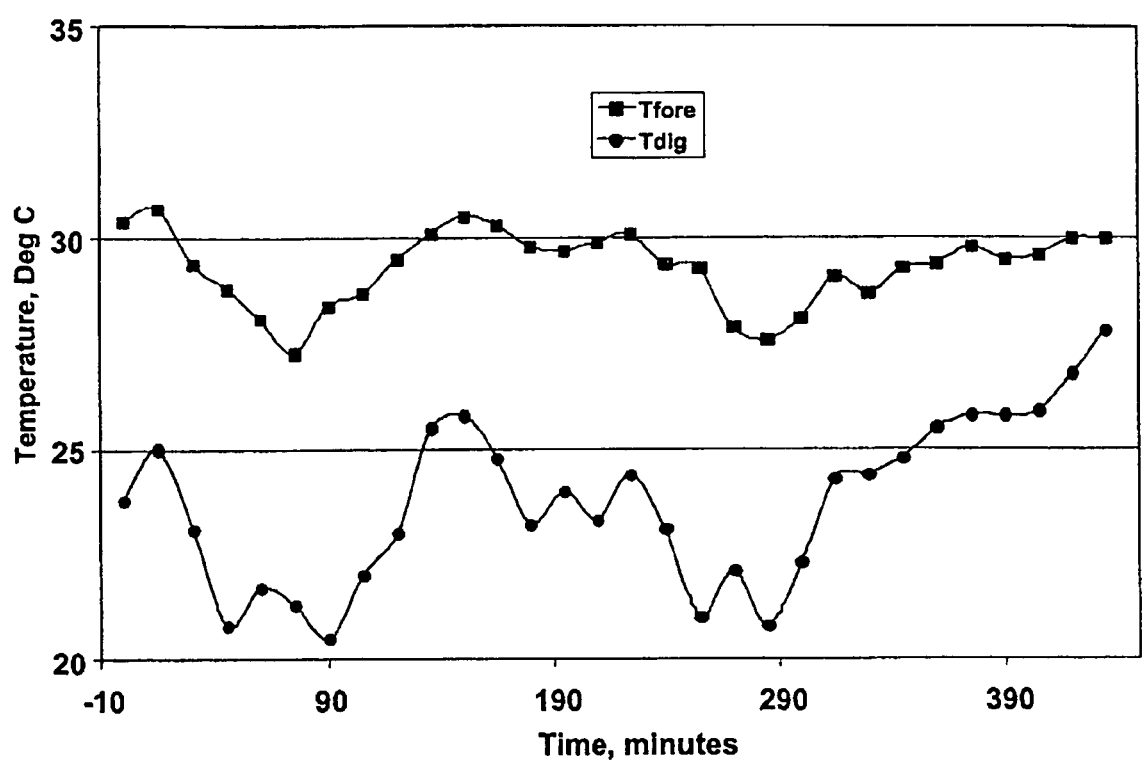
FIG. 13 is a plot over time of forearm temperature (Tfore) and fingertip temperature (Tdig) for subject #33 during Phase 5 testing discussed in the Examples section.
Figure 14:
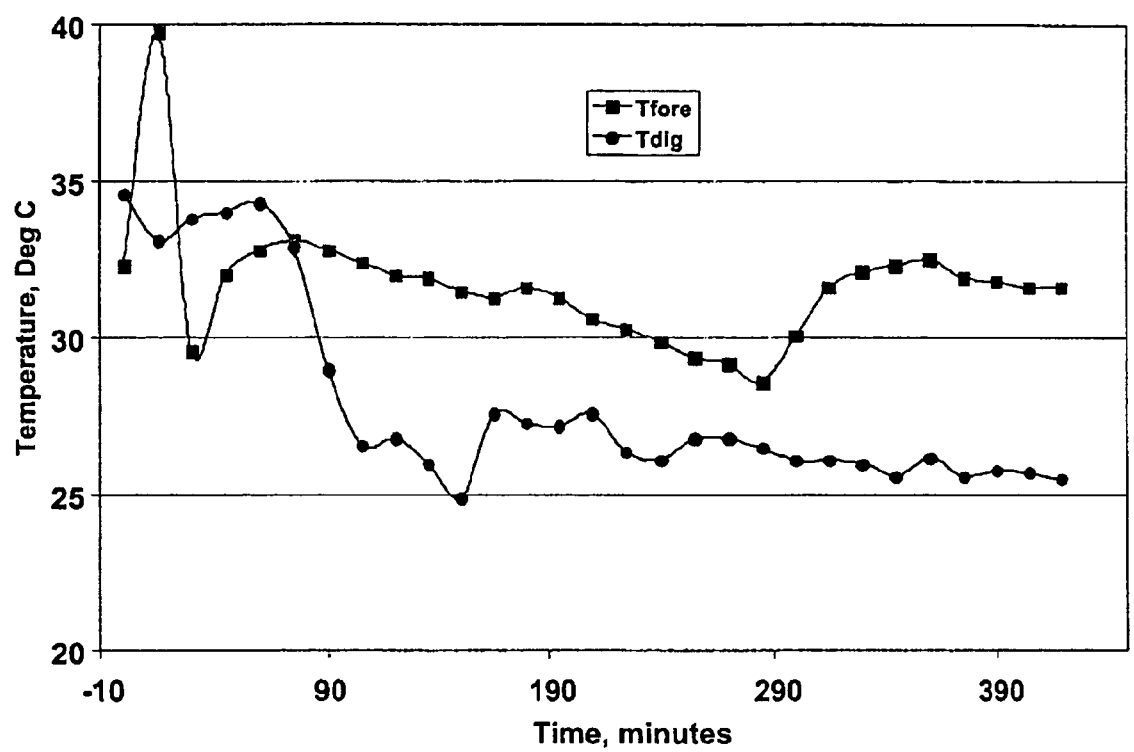
FIG. 14 is a plot over time of forearm temperature (Tfore) and fingertip temperature (Tdig) for subject #34 during Phase 5 testing discussed in the Examples section.
Figure 15:
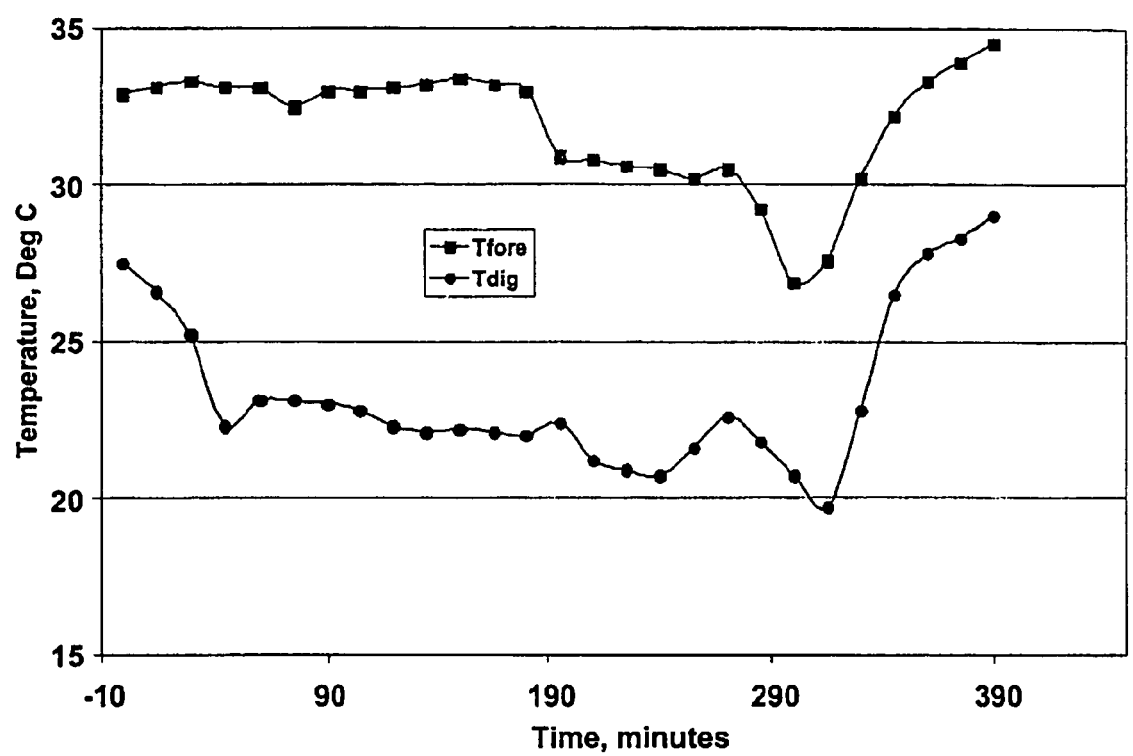
FIG. 15 is a plot over time of forearm temperature (Tfore) and fingertip temperature (Tdig) for subject #35 during Phase 5 testing discussed in the Examples section.
Figure 16:
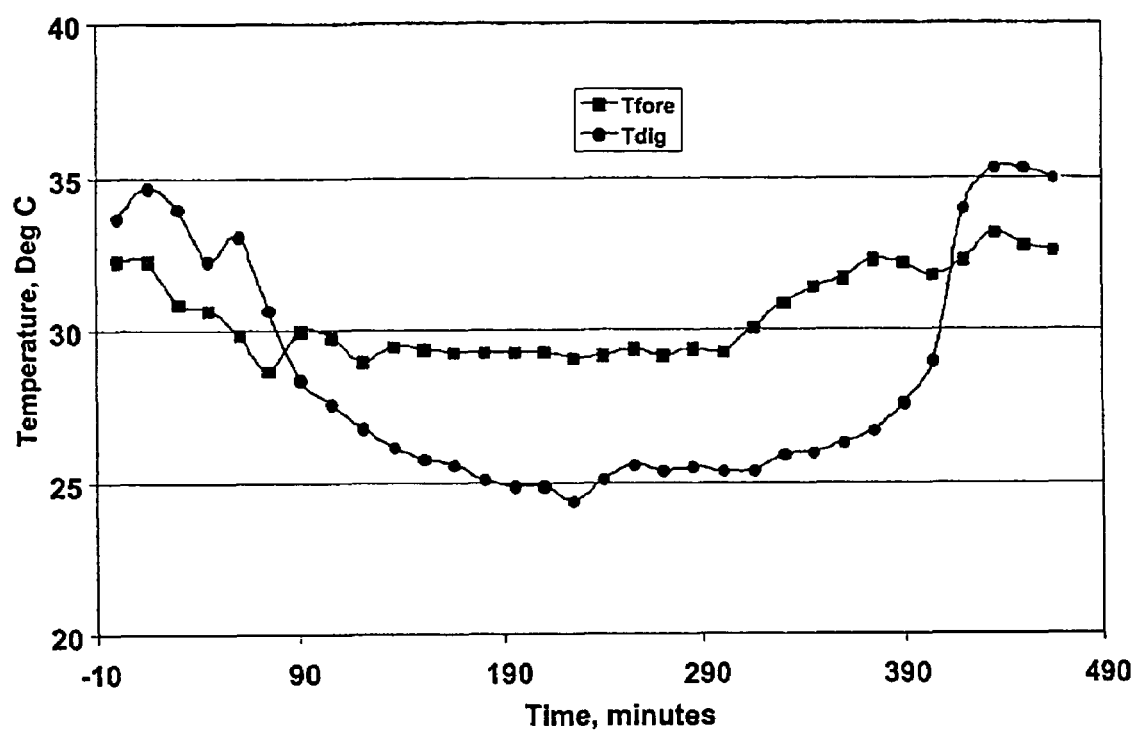
FIG. 16 is a plot over time of forearm temperature (Tfore) and fingertip temperature (Tdig) for subject #37 during Phase 6 testing discussed in the Examples section.
Figure 17:
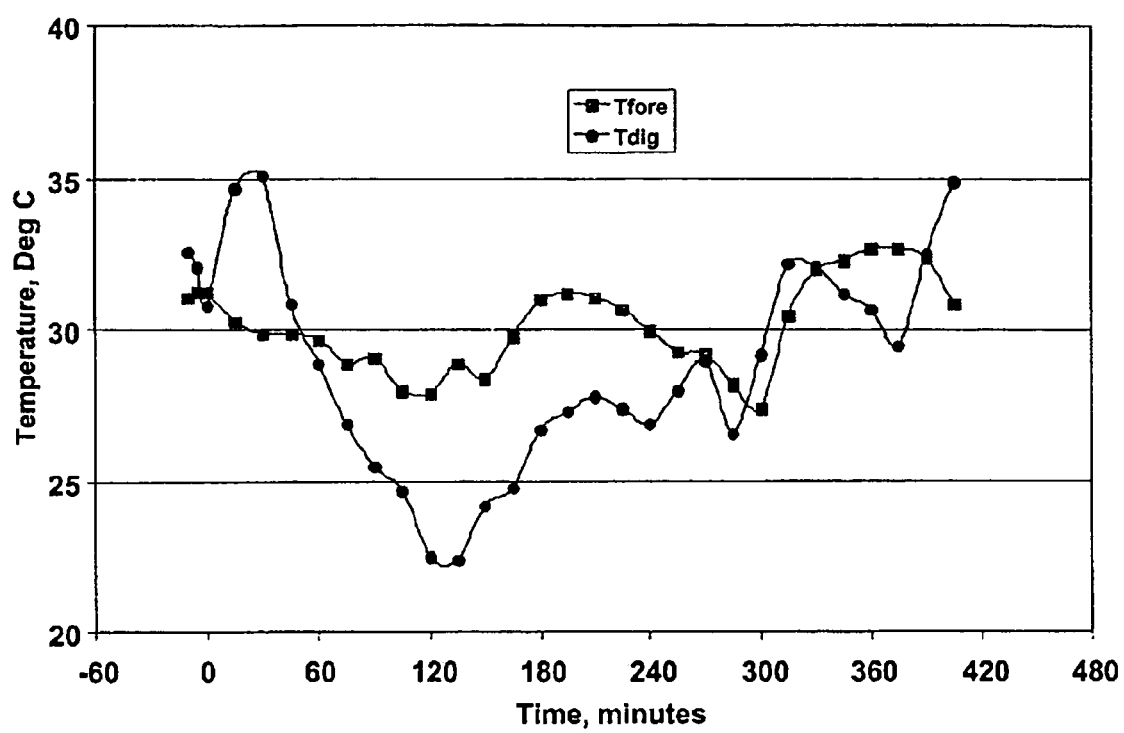
FIG. 17 is a plot over time of forearm temperature (Tfore) and fingertip temperature (Tdig) for subject #38 during Phase 6 testing discussed in the Examples section.
Figure 18:
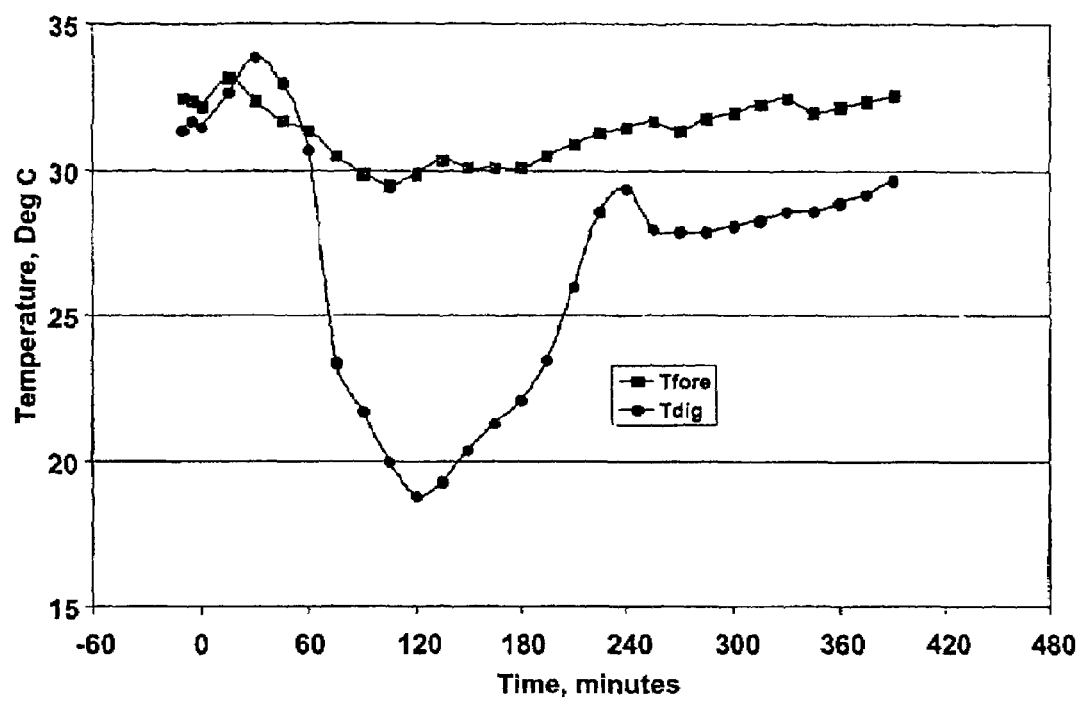
FIG. 18 is a plot over time of forearm temperature (Tfore) and fingertip temperature (Tdig) for subject #39 during Phase 6 testing discussed in the Examples section.
Figure 19:
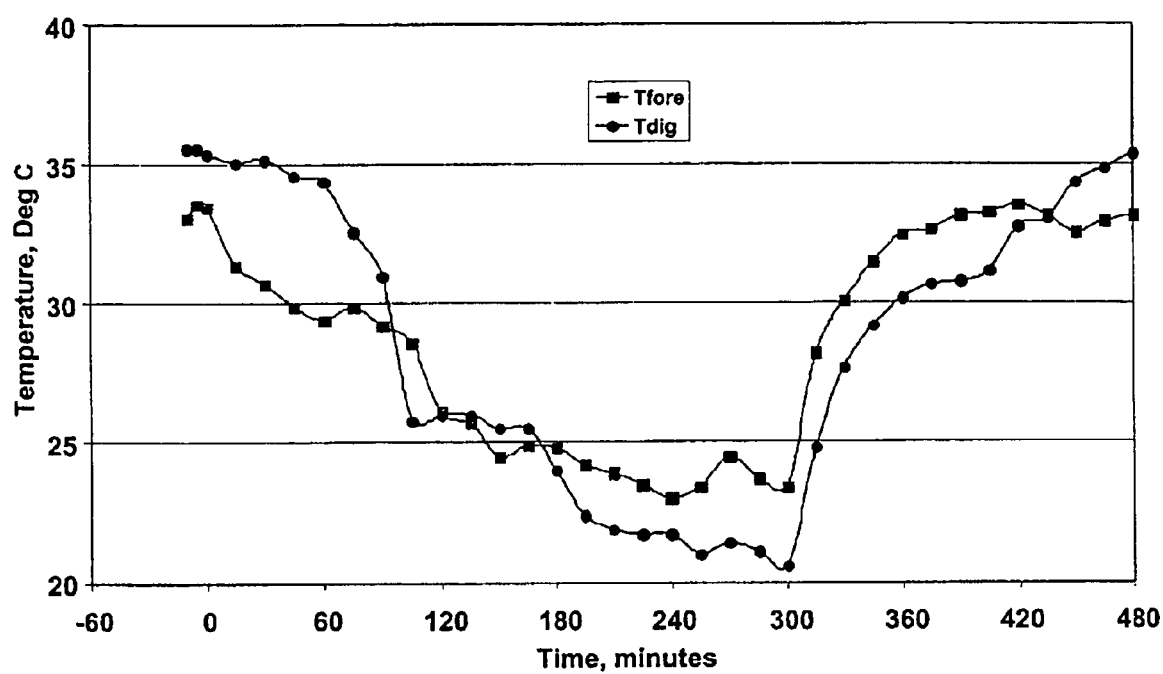
FIG. 19 is a plot over time of forearm temperature (Tfore) and fingertip temperature (Tdig) for subject #40 during Phase 6 testing discussed in the Examples section.
Figure 20:
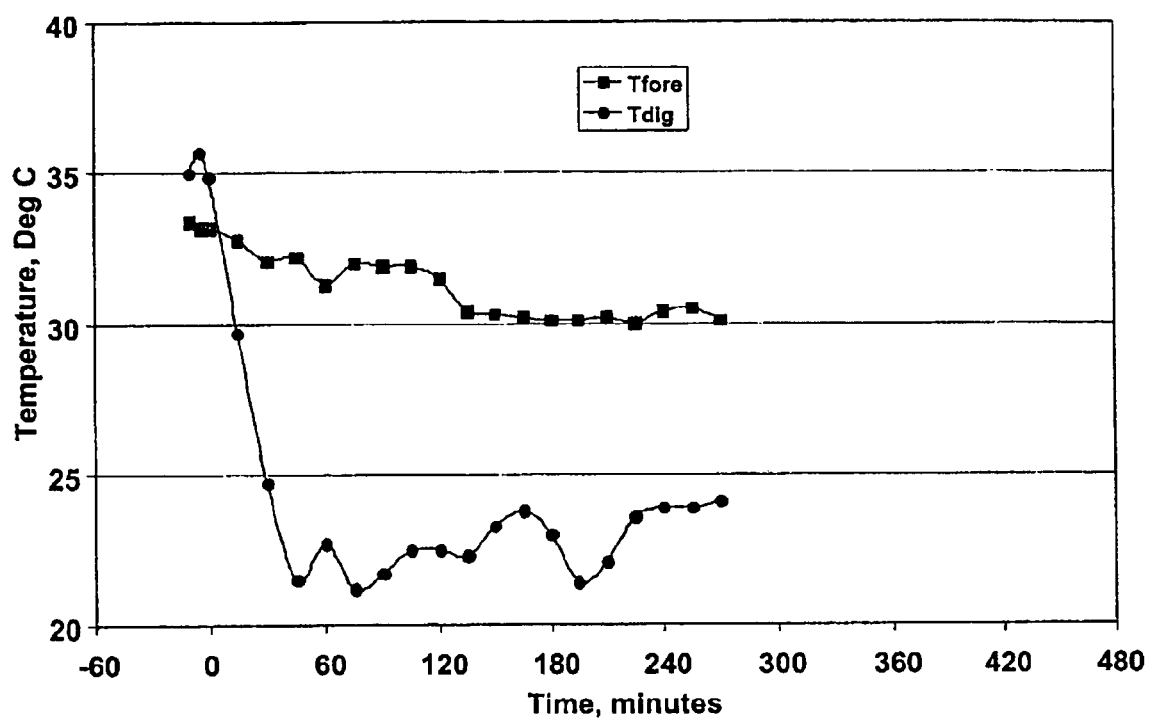
FIG. 20 is a plot over time of forearm temperature (Tfore) and fingertip temperature (Tdig) for subject #41 during Phase 6 testing discussed in the Examples section.
Figure 21:
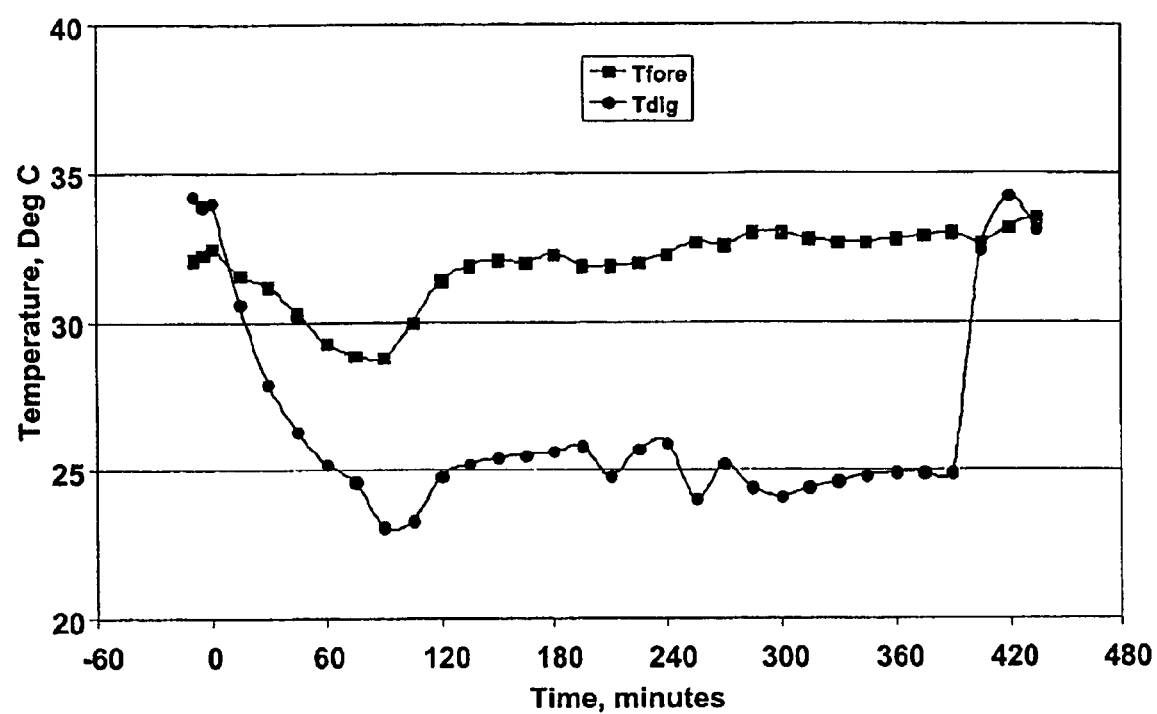
FIG. 21 is a plot over time of forearm temperature (Tfore) and fingertip temperature (Tdig) for subject #42 during Phase 6 testing discussed in the Examples section.
Figure 22:
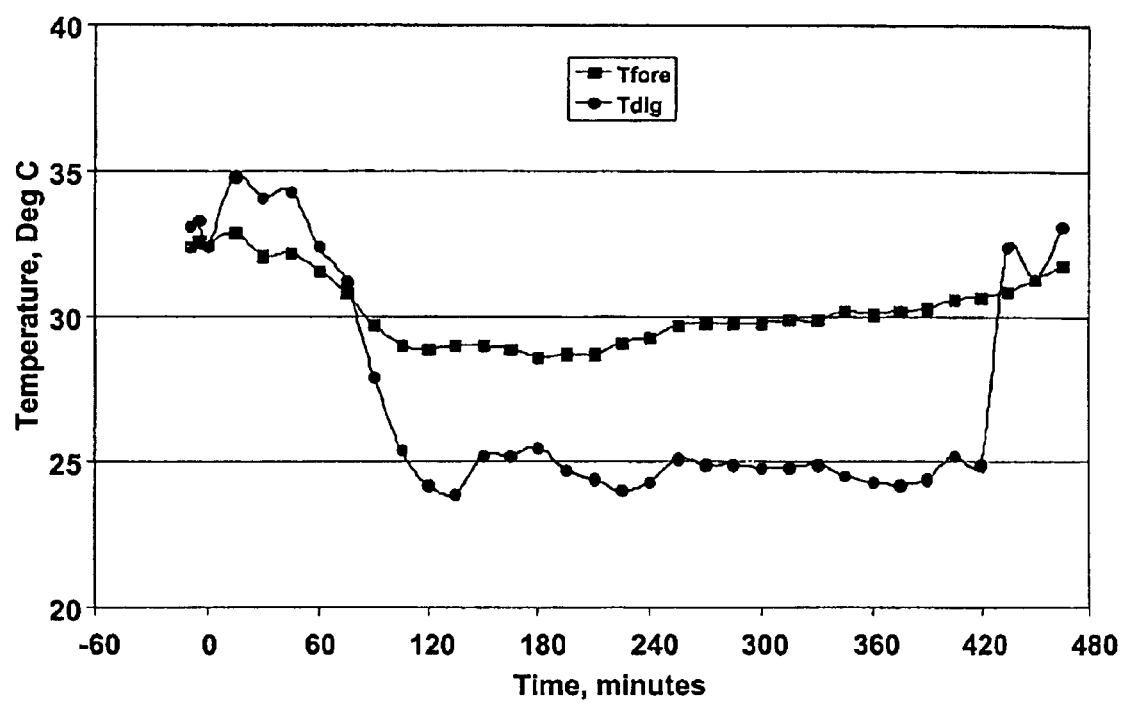
FIG. 22 is a plot over time of forearm temperature (Tfore) and fingertip temperature (Tdig) for subject #43 during Phase 6 testing discussed in the Examples section.
Figure 23:
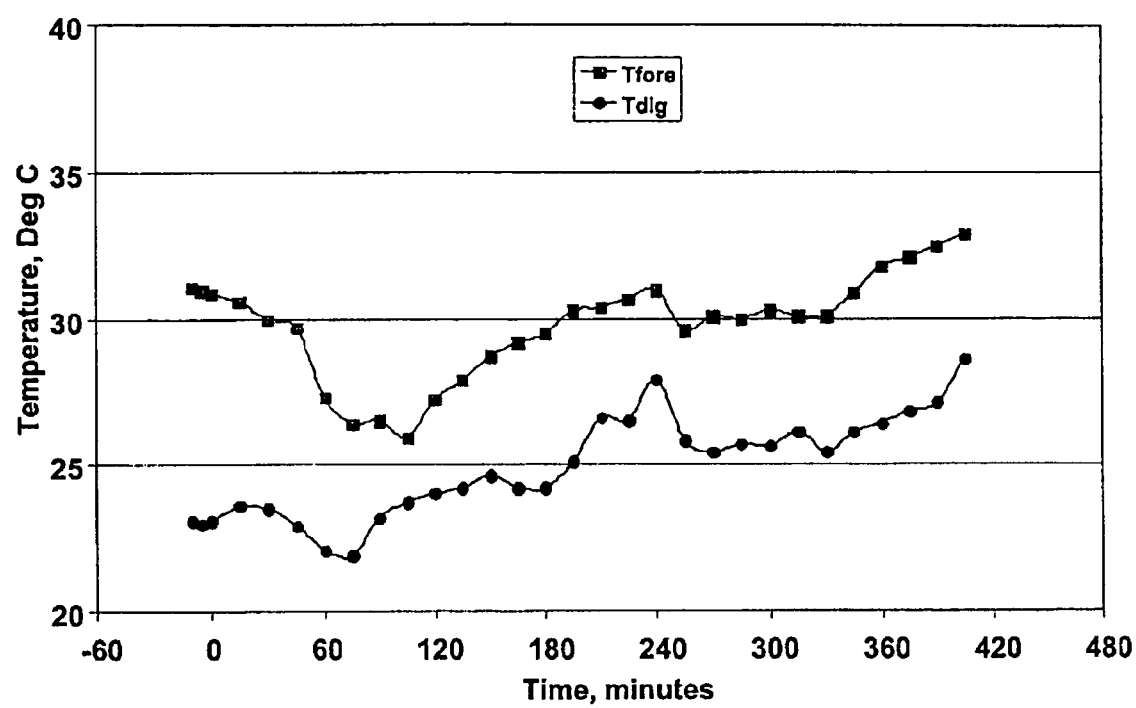
FIG. 23 is a plot over time of forearm temperature (Tfore) and fingertip temperature (Tdig) for subject #44 during Phase 6 testing discussed in the Examples section.

FIGS. 1-23 graphically summarize data concerning patient forearm temperature (Tfore) and fingertips temperature (Tdig) versus time during cooling of subjects during Phases 3a, 4, 5 and 6 described above. For Phases 3a, 4 and 5, indications of vasodilation (Tdig being larger than Tfore) are observed during the early stages of cooling in only a few of the subjects (to varying degrees in subjects #20, #23, #25, #26 #32 and #34). For Phase 6, indications of vasodilation are observed in seven of eight subjects during the early stages of cooling.

The foregoing discussion of the invention has been presented for purposes of illustration and description. The foregoing is not intended to limit the invention to only the form or forms specifically disclosed herein. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described with respect to any disclosed implementation may be combined in any combination with one or more features of any other implementation or implementations. Moreover, the invention specifically includes use of the vasodilation drug, and optionally in combination with one or both of the anti-shivering drug and the anti-emetic drug, (i) in any implementation disclosed herein to induce hypothermia, and (ii) in the manufacture or preparation of a medicament for any treatment disclosed herein to induce hypothermia, and (iii) involving any other manipulation or processing in preparation for any implementation disclosed herein to induce hypothermia.

The terms "comprise", "include", "have" and "contain", and variations of those terms, as may be used in relation to the presence any feature described or claimed, are intended to indicate only that a particular feature is present to an extent as specified, and are not intended to limit the presence of that feature beyond the extent specified or the presence of other features.

What is claimed is:

1. A method for rapid inducement of hypothermia in a human patient, the method comprising:
    cooling the human patient to lower a core temperature of the body of the human patient;
    the cooling comprising, transferring, during a time of two hours or less, a quantity of heat larger than 200 kilocalories from the body of the human patient at a heat transfer rate that is larger than 250 kilocalories per hour for a period of at least 20 minutes, the quantity of heat being transferred across exterior body surface of the human patient to a heat exchange device in heat transfer communication with the exterior body surface;
    administering a vasodilation drug to the human patient to dilate blood vessels in the human patient, at least a portion of the administering occurring between 30 minutes prior to the beginning of the period and the end of the period; and
    administering an anti-shivering drug to the human patient, at least a portion of the administering the anti-shivering drug occurring between 30 minutes prior to the beginning of the period and the end of the period.

2. The method of claim 1, wherein during the period, cumulative heat transfer flux across the exterior body surface in heat transfer communication with the heat exchange device is larger than 125 kilocalories per square meter of the exterior body surface in heat transfer communication with the heat exchange device.

3. The method of claim 2, wherein during the time for transferring the quantity of heat, cumulative heat transfer flux across the exterior body surface in heat transfer communication with the heat exchange device is larger than 500 kilocalories per square meter of the exterior body surface in heat transfer communication with the heat exchange device.

4. The method of claim 3, wherein during the period, cumulative heat transfer flux across the exterior body surface in heat transfer communication with the heat exchange device is larger than 175 kilocalories per square meter of the exterior body surface in heat transfer communication with the heat exchange device.

5. The method of claim 4, wherein during the time for transferring the quantity of heat, the core temperature is reduced by more than 1.0° C.

6. The method of claim 3, wherein the time for transferring the quantity of heat is one hour or less.

7. The method of claim 2, wherein the transferring comprises flowing a heat transfer fluid through the heat exchange device, whereby the quantity of heat is transferred to the heat transfer fluid.

8. The method of claim 7, wherein the heat transfer device comprises a contact cooling pad and the heat transfer fluid is a liquid.

9. The method of claim 8, wherein the liquid comprises water.

10. The method of claim 8, wherein the contact cooling pad comprises an adherent surface in adherent contact with the exterior body surface.

11. The method of claim 1:
wherein during the period, cumulative heat transfer flux across the exterior body surface in heat transfer communication with the heat exchange device is larger than 125 kilocalories per square meter of the exterior body surface in heat transfer communication with the heat exchange device;
wherein the transferring comprises flowing a heat transfer fluid through the heat exchange device, whereby the quantity of heat is transferred to the heat transfer fluid
wherein the heat transfer device comprises a contact cooling pad and the heat transfer fluid is a liquid; and
wherein the contact cooling pad comprises an adherent surface in adherent contact with the exterior body surface and the adherent surface comprises a thermally conductive hydrogel layer.

12. The method of claim 1, wherein the cooling comprises lowering the core temperature of the human patient by at least 1.0° C. during the time for transferring the quantity of heat.

13. The method of claim 1, wherein the cooling comprises reducing the core temperature in an amount in a range of from 1.0° C. to 5° C. during the time for transferring the quantity of heat.

14. The method of claim 13 wherein the cooling comprises reducing the core temperature to below 35.0° C. during the time for transferring the quantity of heat.

15. The method of claim 1, wherein the human patient exhibits systemic vasodilation during at least a portion of the period.

16. The method of claim 1, wherein the vasodilation drug comprises one or both of nitroprusside and nitroglycerin.

17. The method of claim 1, wherein the vasodilation drug comprises a magnesium salt.

18. The method of claim 17, wherein the magnesium salt comprises magnesium sulfate.

19. The method of claim 18, wherein the administering the vasodilation drug comprises administration of an initial dose of at least two grams of the magnesium salt prior to the end of the period.

20. The method of claim 19, wherein the administering the vasodilation drug comprises continuous maintenance administration of the magnesium salt during at least a portion of the cooling that follows the period.

21. The method of claim 20, wherein the continuous maintenance administration is at a rate of at least one gram per hour continuing for at least two hours.

22. The method of claim 1, wherein the anti-shivering drug comprises an opioid analgesic.

23. The method of claim 22, wherein the opioid analgesic is meperidine.

24. The method of claim 22, wherein the vasodilation drug is a magnesium salt.

25. The method of claim 24, wherein the anti-shivering drug is meperidine.

26. The method of claim 25, wherein the vasodilation drug is magnesium sulfate.

27. The method of claim 1, wherein the vasodilation drug comprises niacin.

28. A method of for rapid inducement of hypothermia in a human patient, the method comprising:
cooling the human patient to lower a core temperature of the body of the human patient;
the cooling comprising, transferring, during a time of two hours or less, a quantity of heat larger than 200 kilocalories from the body of the human patient at a heat transfer rate that is larger than 250 kilocalories per hour for a period of at least 20 minutes, the quantity of heat being transferred to a heat exchange device in heat transfer communication with the body;
administering a vasodilation drug to the human patient to dilate blood vessels in the human patient, at least a portion of the administering occurring between 30 minutes prior to the beginning of the period and the end of the period;
administering an anti-shivering drug comprising an opioid analgesic to the human patient, at least a portion of the administering the anti-shivering drug occurring between 30 minutes prior to the beginning of the period and the end of the period; and
administering an anti-emetic drug to the human patient, at least a portion of the administering the anti-emetic drug occurring between 30 minutes prior to the beginning of the period and the end of the period.

29. The method of claim 28, wherein the anti-emetic drug comprises a Serotonin 5-$HT_3$ antagonist.

30. The method of claim 29, wherein the administering the anti-emetic drug is commenced prior to commencement of the administering the anti-shivering drug and prior to the commencement of the administering the vasodilation drug.

31. The method of claim 29, wherein:
the vasodilation drug comprises one or more of the following: a magnesium salt and niacin; and
the anti-shivering drug comprises meperidine.

32. The method of claim 31, wherein the quantity of heat is larger than 300 kilocalories and the heat transfer rate is larger than 350 kilocalories per hour.

* * * * *